United States Patent
Eroglu et al.

(10) Patent No.: US 10,429,374 B2
(45) Date of Patent: Oct. 1, 2019

(54) GENETICALLY ENCODED POTASSIUM ION INDICATORS

(71) Applicant: Medizinische Universität Graz, Graz (AT)

(72) Inventors: Emrah Eroglu, Eichgraben (AT); Helmut Bischof, Graz (AT); Wolfgang Graier, Judendorf Strassengel (AT); Roland Malli, Gleinstätten (AT); Markus Waldeck-Weiermair, Graz (AT)

(73) Assignee: MEDIZINISCHE UNIVERSITÄT GRAZ, Braz (AT)

( * ) Notice: Subject to any disclaimer, the term of this patent is extended or adjusted under 35 U.S.C. 154(b) by 0 days.

(21) Appl. No.: 15/975,427

(22) Filed: May 9, 2018

(65) Prior Publication Data

US 2018/0328908 A1 Nov. 15, 2018

(30) Foreign Application Priority Data

May 11, 2017 (AT) .............. A 50400/2017

(51) Int. Cl.
*G01N 33/52* (2006.01)
*G01N 33/487* (2006.01)
*C12N 15/63* (2006.01)
*C07K 14/00* (2006.01)
*G01N 33/50* (2006.01)
*G01N 33/49* (2006.01)
*G01N 33/542* (2006.01)
*G01N 33/84* (2006.01)

(52) U.S. Cl.
CPC ....... *G01N 33/48721* (2013.01); *C07K 14/00* (2013.01); *C07K 14/001* (2013.01); *C12N 15/63* (2013.01); *G01N 33/4875* (2013.01); *G01N 33/492* (2013.01); *G01N 33/5067* (2013.01); *G01N 33/523* (2013.01); *G01N 33/542* (2013.01); *G01N 33/84* (2013.01); *C07K 2319/02* (2013.01)

(58) Field of Classification Search
None
See application file for complete search history.

(56) References Cited

U.S. PATENT DOCUMENTS

2011/0091919 A1    4/2011 Ye et al.

FOREIGN PATENT DOCUMENTS

JP    2011097930    5/2011

OTHER PUBLICATIONS

Hennigan, Robert F. et al, "a fret-based approach for studying conformational changes of a cytoskeleton-related tumor suppressor molecule." Methods Mol. Biol. (2009) 586 (chapter 7) p. 143-156.*
Ashraf Ku, et al., "The Potassium Binding Protein Kbp is a Cytoplasmic Potassium Sensor". Structure. May 3, 2016;24(5):741-749.
Ameen S, et al., "Designing, construction and characterization of genetically encoded FRET-based nanosensor for real time monitoring of lysine flux in living cell". J Nanobiotechnology. Jun. 22, 2016;14 (1): 49.
Bischof H, et al., Novel genetically encoded fluorescent probes enable real-time detection of potassium in vitro and in vivo. Nat Commun. Nov. 10, 2017;8(1):1422.

* cited by examiner

*Primary Examiner* — Fred H Reynolds
(74) *Attorney, Agent, or Firm* — Pepper Hamilton LLP

(57) ABSTRACT

The present invention relates to a polypeptide comprising at least one signaling domain and a potassium sensor which is capable of binding K$^+$ and the first signaling domain is capable of generating a detectable signal upon binding of K$^+$ to the potassium sensor. The invention also relates to a polynucleotide encoding said polypeptide and the use of the polypeptide in various applications for the detection of K$^+$.

19 Claims, 7 Drawing Sheets

Specification includes a Sequence Listing.

GENETICALLY ENCODED POTASSIUM ION INDICATORS

CROSS-REFERENCE TO RELATED PATENT APPLICATIONS

This application claims priority to Austrian Patent Application No. A50400/2017, filed May 11, 2017, which is incorporated by reference in its entirety.

SEQUENCE LISTING

The instant application contains a Sequence Listing which has been submitted electronically in ASCII format and is hereby incorporated by reference in its entirety. Said ASCII copy, created on May 30, 2019, is named 146998_00301_SL.txt and is 35,234 bytes in size.

BACKGROUND OF THE INVENTION

Potassium ions ($K^+$) are necessary for the proper functioning of all cell types. Electrochemical $K^+$ gradients across the plasma membrane and membranes of cellular organelles drive $K^+$ fluxes to control a variety of cell functions. It is well known that fluctuations of the extra- and intracellular $K^+$ concentration control muscle contraction, neurotransmitter and hormone release, neuronal excitability, cell volume, cell proliferation, and cell death. Hence, it is not surprising, that an imbalance of the $K^+$ homeostasis has profound implications at both the cellular and organismal level and is associated with a host of pathological conditions including neurological-, cardio-vascular-, renal-, immunological-, muscle-, and metabolic disorders as well as cancer. $K^+$ fluxes and transport across biomembranes are accomplished by numerous selective $K^+$-channels, exchangers and pumps which emerged as promising therapeutic drug targets for the treatment of various diseases. Our present understanding of extra- and intracellular $K^+$ fluctuations is, however, very limited due to the lack of applicable probes to investigate $K^+$ dynamics with high spatial and temporal resolution.

Strikingly, there is emerging evidence that the $K^+$ concentration within cells control key signaling events also independently from its impact on the membrane potential.

In a recent study, increased intracellular $K^+$ levels were shown to augment the activity of the phosphatase PP2A in T-cells (Eil et al., Nature 537, 539-543 (22 Sep. 2016). As a consequence the Akt-mTOR complex is hypo-phosphorylated and the T-cell effector function suppressed. This study unveils how tightly fundamental cell functions are controlled by $K^+$ ions independently of their contribution to the membrane potential. Moreover, the distribution of $K^+$ among cellular organelles and how dynamic and strong inner organelle $K^+$ concentrations might be affected under certain physiological and pathological conditions have so far not been investigated comprehensively. Our knowledge in this regard is very poor mainly due to a lack of suitable methods and tools that allow quantifying $K^+$ fluxes on the level of individual cells and cellular organelles in real-time. Currently, $K^+$ sensitive electrodes are often used to measure extracellular $K^+$ fluctuations and typically require relatively large sample volumes of at least 1 ml. These electrodes are highly selective for $K^+$ but they can hardly be used to detect the spatiotemporal dynamics of $K^+$ fluctuations and intracellular $K^+$ signals. Several small chemical fluorescent $K^+$ sensors have been developed with the aim to either image extracellular $K^+$ fluctuations or changes of $K^+$ within cells. However, these fluorescent ionic indicators have many limitations as they are often less specific for $K^+$, show a low dynamic range, are $K^+$ sensitive in a non-physiological range, difficult to load into cells and cellular organelles, and in some cases difficult to obtain.

Due to these many severe limitations of fluorescent $K^+$ probes, a meaningful quantitative $K^+$ imaging using fluorescence microscopy and/or fluorimeters is virtually impossible.

Ashraf et al. disclose that a potassium binding protein (Kbp) may in vivo act as a cytoplasmic potassium sensor that is required for normal growth of E. coli at high $K^+$ concentrations. (Structure 2016, May 3; 24(5) 741-9).

WO 01/04623 A1 discloses fluorescence-marked cyclic peptolides (depsipeptides) and their use for optically determining the concentration of potassium ions in a sample.

US 2013/244891 A1 discloses a biosensor comprising an activatable acceptor fluorogen linked by a linker to an environment-sensitive donor that interacts with an analyte.

WO 2012/112440 A2 discloses a fluorescent co-polymer that may function as a potassium ion sensor.

US 2003/119195 A1 discloses fluorescent anthrazene-based fluoroionophores as potassium sensors.

In the light of this prior art, there is still a need to provide further $K^+$ sensors. The development of such sensors is challenging since for example the construction of proximity-based probes is challenging. So far, it cannot be reliably predicted whether the steric effects in a genetically encoded sensor due to ligand binding may induce a conformational change that can be detectable, e.g. by fluorescence quenching or Førster Energy Resonance Transfer (FRET). The suitability of a genetically encoded sensor thus depends on a case-by-case basis on the individual binding domain, the extend and stability of its conformational change upon ligand binding and optional linker sequence between the binding module and the detection domains.

Thus, it is an object of the present invention to provide novel agents suitable for the detection of $K^+$.

Further, it is another object of the present invention to provide novel methods for detecting $K^+$ in a sample.

SUMMARY

The objects of the present invention are solved by a polypeptide comprising:
  a) a first signaling domain, and
  b) a potassium sensor comprising
     b1) a first domain of the potassium sensor comprising an amino acid sequence which exhibits at least 70% identity to the sequence according to SEQ ID NO: 1; and
     b2) a second domain of the potassium sensor comprising an amino acid sequence which exhibits at least 70% identity to the sequence according to SEQ ID NO: 2;
  wherein the potassium sensor is capable of binding positively charged potassium ion and the first signaling domain is capable of generating a detectable signal upon binding of positively charged potassium ions to the potassium sensor.

In one aspect, the present invention relates to a polynucleotide encoding for a polypeptide suitable for the detection of $K^+$.

In one aspect, the present invention relates to a vector encoding the inventive polypeptide suitable for eukaryotic or prokaroytic gene expression.

In another aspect, the present invention relates to a cell comprising the inventive polynucleotide, vector or polypeptide.

In a further aspect, the present invention relates to a method for detecting positively charged potassium ions in a sample, comprising the steps of
- a) providing the inventive polypeptide;
- b) contacting the polypeptide of the present invention with the sample;
- c) measuring the signal generated by the first signaling domain; and/or
- d) measuring the signal generated together by the first signaling domain and the second signaling domain;

wherein a change in signal intensity after contact with the sample indicates the presence of the potassium ions in the sample.

In a further aspect, the present invention relates to the use of a polypeptide according to the present invention for detecting a positively charged potassium ion in a sample.

In yet another aspect, the present invention relates to a kit for detecting positively charged potassium ions.

BRIEF DESCRIPTION OF FIGURES

FIG. 3 shows the distance between the two closest acidic amino acids. Under (d), FIG. 3 shows the predicted pore diameter with the $K^+$ ion, followed by (e) $K^+$ ion radius with and without hydration.

DETAILED DESCRIPTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Although several documents are cited throughout the text of this specification, which are incorporated by reference in their entirety, nothing herein is to be construed as an admission that the invention is not entitled to antedate such disclosure by virtue of prior invention.

The $K^+$ binding protein (Kbp), also known as YgaU, is a soluble 16-kDa cytoplasmic protein from *Escherichia coli*. It is a highly specific $K^+$ binding protein and is required for normal growth in the presence of high levels of external $K^+$. The potassium ion binds exclusively to the BON domain (SEQ ID NO:1), which upon binding undergoes a conformational change. Kbp further comprises the LysM domain (SEQ ID NO: 2) which may interact with the BON domain.

The amino acid sequences of the BON domain, LysM domain as well as the full length Kbp are shown below in Table 1.

TABLE 1

Sequences of BON domain and LysM domain of Kbp

| SEQ ID NO: | Comment | Amino acid sequence |
|---|---|---|
| 1 | BON domain | QAKKVQEHLNKTGIPDADKVNIQIADGKATVTGDGL SQEAKEKILVAVGNISGIASVDDQVKT |
| 2 | LysM domain | QFYTVKSGDTLSAISKQVYGNANLYNKIFEANKPML KSPDKIYPGQVLRI |

It has surprisingly been found that $K^+$ may be detected by a fusion protein comprising a) a first signaling domain, and
b) a potassium sensor comprising
  b1) a first domain of the potassium sensor comprising an amino acid sequence which exhibits at least 70% identity to the sequence according to SEQ ID NO: 1; and
  b2) a second domain of the potassium sensor comprising an amino acid sequence which exhibits at least 70% identity to the sequence according to SEQ ID NO: 2;
wherein the potassium sensor is capable of binding positively charged potassium ion and the first signaling domain is capable of generating a detectable signal upon binding of positively charged potassium ion to the potassium sensor.

Figure 1:
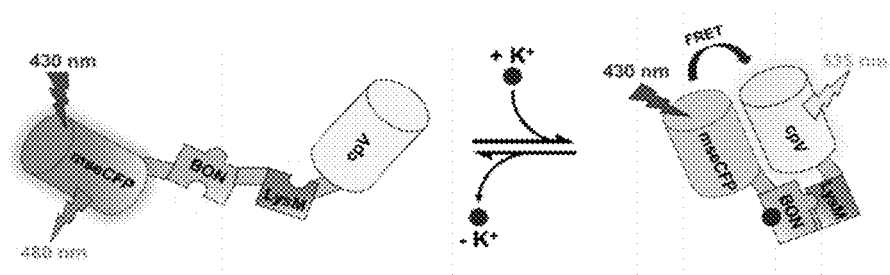
FIG. 1 shows a schematic overview of the conformational change in the polypeptide upon binding of $K^+$ to the BON domain, which increases the detectable FRET signal.

The binding of $K^+$ to the potassium sensor may trigger a conformational change in said potassium sensor which may then be detected via the signaling domain. This principle is illustrated for one of the polypeptide of the present invention in FIG. 1. The polypeptides according to the invention are also called herein Genetically Encoded Potassium Ion Indicator (GEPII).

In a preferred embodiment, the first signaling domain is a fluorescent protein domain. It is even more preferred that the first signaling domain is a cyan fluorescent protein, preferably a cyan fluorescent protein which may comprise an amino acid sequence of SEQ ID NO:6 or an amino acid sequence of at least 70%, 80%, 85%, 90%, 95% or 100% identity to the sequence according to SEQ ID NO:6.

In a preferred embodiment, the first signaling domain is a fluorescent protein domain. Without being bound to theory, the detectable signal generated by the first signaling may be a quenching of the fluorescence signal of the fluorescent protein domain. In one preferred embodiment, the amino acid sequence of the polypeptide of the present invention comprises from N-terminus to C-terminus:
i) the first domain of the potassium sensor;
ii) the first signaling domain; and
iii) the second domain of the potassium sensor.

The first signaling domain may optionally be preceded and/or followed by a linker sequence.

In yet another preferred embodiment, the amino acid sequence of the polypeptide of the present invention comprises from N-terminus to C-terminus: i) the first domain of the potassium sensor;
i) the second domain of the potassium sensor;
ii) the first signaling domain; and
iii) the first domain of the potassium sensor.

The first signaling domain may optionally be preceded and/or followed by a linker sequence.

The first domain of the potassium sensor is based on the BON domain of Kbp.

In a preferred embodiment, the first domain of the potassium sensor comprises an amino acid sequence which exhibits at least 75% identity to the sequence according to SEQ ID NO:1. In one preferred embodiment, the first domain of the potassium sensor comprises an amino acid sequence which exhibits at least 80% identity to the sequence according to SEQ ID NO:1. In one preferred embodiment, the first domain of the potassium sensor comprises an amino acid sequence which exhibits at least 85% identity to the sequence according to SEQ ID NO:1. In one preferred embodiment, the first domain of the potassium sensor comprises an amino acid sequence which exhibits at least 90% identity to the sequence according to SEQ ID NO:1. In one preferred embodiment, the first domain of the potassium sensor comprises an amino acid sequence which exhibits at least 95% identity to the sequence according to SEQ ID NO:1. In another preferred embodiment, the first domain of the potassium sensor comprises an amino acid sequence which exhibits at least 100% identity to the sequence according to SEQ ID NO:1.

In another preferred embodiment, the first domain of the potassium sensor comprises an amino acid sequence of SEQ ID NO:1 with at least one amino acid substitution. Preferably, the amino acid sequence of SEQ ID NO: 1 comprises from about 1 to about 11 substitutions. In a preferred embodiment, the at least one amino acid substitution is selected from the group consisting of D41N, D43N, D51N, D59N, E64Q, D83N, D84N, Q26R, N35Q, N75Q, or G52D. In a particularly preferred embodiment, the potassium sensor comprises an amino acid sequence for the first domain of the potassium sensor of SEQ ID NO: 01 having the following substitutions: Q26R, N35Q, N75Q, G52D (SEQ ID NO: 5).

The second domain of the potassium sensor is based on the LysM domain of Kbp. In a preferred embodiment, the second domain of the potassium sensor comprises an amino acid sequence which exhibits at least 75% identity to the sequence according to SEQ ID NO:2. In one preferred embodiment, the second domain of the potassium sensor comprises an amino acid sequence which exhibits at least 80% identity to the sequence according to SEQ ID NO:2. In one preferred embodiment, the second domain of the potassium sensor comprises an amino acid sequence which exhibits at least 85% identity to the sequence according to SEQ ID NO:2. In one preferred embodiment, the second domain of the potassium sensor comprises an amino acid sequence which exhibits at least 90% identity to the sequence according to SEQ ID NO:2. In one preferred embodiment, the second domain of the potassium sensor comprises an amino acid sequence which exhibits at least 95% identity to the sequence according to SEQ ID NO:2. In another preferred embodiment, the second domain of the potassium sensor comprises an amino acid sequence which exhibits at least 100% identity to the sequence according to SEQ ID NO:2.

In another preferred embodiment, the second domain of the potassium sensor comprises an amino acid sequence of SEQ ID NO:2 with at least one amino acid substitution. In a preferred embodiment, the second domain of the potassium sensor comprises an amino acid sequence of SEQ ID NO:2 comprising from about 1 to about 11 substitutions. In a preferred embodiment, the at least one amino acid substitution is selected from the group consisting of D104N, E125Q, D135N, N116Q, N118Q, N121Q and N127Q. In a particularly preferred embodiment, the potassium sensor comprises an amino acid sequence of the second domain of the potassium sensor of SEQ ID NO:2 having the following substitutions: D104N, E125Q, D135N (SEQ ID NO:4). The numbering of the amino acids in the sequence is based on the wild type sequence of Kbp (SEQ ID NO:3).

Table 2 summarizes respective amino acid sequences of Kbp and variants of the BON and Lys domains.

TABLE 2

Kbp and variants of BON and Lys domains

| SEQ ID NO: | Comment | Amino acid sequence |
|---|---|---|
| 3 | Kbp | MGLFNFVKDAGEKLWDAVTGQHDKDDQAKKVQEHLN KTGIPDADKVNIQIADGKATVTGDGLSQEAKEKILV AVGNISGIASVDDQVKTATPATASQFYTVKSGDTLS AISKQVYGNANLYNKIFEANKPMLKSPDKIYPGQVL RIPEE |
| 4 | LysM D104N, E125Q, D135N | QFYTVKSGNTLSAISKQVYGNANLYNKIFQANKPML KSPNKIYPGQVLRI |
| 5 | BON Q26R, N35Q, N75Q, G52D | QAKKVQEHLQKTGIPDADKVNIQIADDKATVTGDGL SQEAKEKILVAVGQISGIASVDDQVKT |

The present invention also relates to a polypeptide comprising
  a) a first signaling domain, and
  b) a potassium sensor comprising
    b1) a first domain of the potassium sensor comprising an amino acid sequence which exhibits at least 70% identity to the sequence according to SEQ ID NO:1; and
    b2) a second domain of the potassium sensor comprising an amino acid sequence which exhibits at least 70% identity to the sequence according to SEQ ID NO:2; and
  c) a second signaling domain,
wherein the potassium sensor is capable of binding positively charged potassium ion and the first signaling domain and the second signaling domain together are capable of generating a detectable signal upon binding of positively charged potassium ion to the potassium sensor. Preferably, the detectable signal may be generated upon binding of $K^+$ to the potassium sensor. The binding of $K^+$ may for example induce a conformational shift in the potassium sensor and then bring the first signaling domain and the second signaling domain in closer proximity or further away from each other, thereby at least contributing to generating the detectable signal. In a preferred embodiment, the first signaling domain and the second signaling domain are together selected from the group consisting of FRET-donor-acceptor pairs, split-enzyme pairs or split-fluorescent protein pairs, wherein the first signaling domain and the second signaling domain are the respective parts of a pair (for example, two halves of a split-enzyme or two halves of a split-fluorescent protein). Preferably, the binding of $K^+$ to the potassium sensor may induce a conformational shift in the polypeptide and the first signaling domain and the second signaling domain may then be capable to generate the detectable signal, e.g. the FRET-donor-acceptor pair may generate a detectable FRET signal, the two halves of a split-enzyme may be functional and catalyze a reaction that may generate a detectable signal or the two halves of a split-fluorescent protein will be capable of emitting light with a specified wavelength as a detectable signal if excited with light with a wavelength within the appropriate range.

In a preferred embodiment, the first signaling domain and the second signaling domain are a FRET-donor-acceptor pair. Preferably, the donor may be a cyan fluorescent protein (CFP) domain and the acceptor may be a yellow fluorescent protein (YFP) domain. More preferably, the first signaling domain may be the donor and the second signaling domain may be the acceptor. In an even more preferred embodiment, the first signaling domain is the donor CFP domain and the second signaling domain is the acceptor YFP domain. It is also preferred that the CFP domain may comprise an amino acid sequence of SEQ ID NO:6 or an amino acid sequence of at least 70%, 80%, 85%, 90%, 95% or 100% identity to the sequence according to SEQ ID NO:6, wherein the excitation wavelength and the fluorescence emission wavelength are the same or substantially the same as for CFP domain according to SEQ ID NO:6, namely with an excitation peak at a wavelength of about 436 nm and an emission peak at a wavelength of about 477 nm. Preferably, the YFP domain may be the circularly permuted venus (CPV) protein which even more preferably comprises an amino acid sequence of SEQ ID NO:7 or an amino acid sequence of at least 70%, 80%, 85%, 90%, 95% or 100% identity to the sequence according to SEQ ID NO:7, wherein the excitation wavelength and the fluorescence emission wavelength are the same or substantially the same as for YFP domain according to SEQ ID NO:7, namely an excitation peak at a wavelength of about 514 nm and an emission peak at about 527 nm.

In another preferred embodiment, the donor may be a Clover domain and the acceptor may be an mRuby2 domain. More preferably, the first signaling domain may be the donor and the second signaling domain may be the acceptor. It is also preferred that the Clover domain may comprise an amino acid sequence of SEQ ID NO:8 or an amino acid sequence of at least 70%, 80%, 85%, 90%, 95% or 100% identity to the sequence according to SEQ ID NO:8, wherein the excitation wavelength and the fluorescence emission wavelength are the same or substantially the same as for the Clover domain according to SEQ ID NO:8, namely with an excitation peak at a wavelength of about 505 nm and an emission peak at a wavelength of about 515 nm. Preferably, the mRuby 2 domain comprises an amino acid sequence of SEQ ID NO:9 or an amino acid sequence of at least 70%, 80%, 85%, 90%, 95% or 100% identity to the sequence according to SEQ ID NO:9, wherein the excitation wavelength and the fluorescence emission wavelength are the same or substantially the same as for mRuby2 domain according to SEQ ID NO:9, namely an excitation peak at a wavelength of about 559 nm and an emission peak at about 600 nm.

Table 3 shows the amino acid sequences of SEQ ID NO: 6 to 9.

TABLE 3

Amino acid sequences of signaling domains

| SEQ ID NO: | Comment | Amino acid sequence |
|---|---|---|
| 6 | mseCFP | MVSKGEELFTGVVPILVELDGDVNGHRFSVSGEGEGD ATYGKLTLKFICTTGKLPVPWPTLVTTLTWGVQCFAR YPDHMKQHDFFKSAMPEGYVQERTIFFKDDGNYKTRA EVKFEGDTLVNRIELKGIDFKEDGNILGHKLEYNYIS HNVYITADKQKNGIKAHFKIRHNIEDGGVQLADHYQQ NTPIGDGPVLLPDNHYLSTQSKLSKDPNEKRDHMVLL EFVTAA |
| 7 | cpV | MDGGVQLADHYQQNTPIGDGPVLLPDNHYLSYQSKLS KDPNEKRDHMVLLEFVTAAGITLGMDELYKGGSGGMV SKGEELFTGVVPILVELDGDVNGHKFSVSGEGEGDAT YGKLTLKLICTTGKLPVPWPTLVTTLGYGLQCFARYP DHMKQHDFFKSAMPEGYVQERTIFFKDDGNYKTRAEV KFEGDTLVNRIELKGIDFKEDGNILGHKLEYNYNSHN VYITADKQKNGIKANFKIRHNIE |
| 8 | Clover | MVSKGEELFTGVVPILVELDGDVNGHKFSVRGEGEGD ATNGKLTLKFICTTGKLPVPWPTLVTTFGYGVACFSR YPDHMKQHDFFKSAMPEGYVQERTISFKDDGTYKTRA EVKFEGDTLVNRIELKGIDFKEDGNILGHKLEYNFNS HNVYITADKQKNGIKANFKIRHNVEDGSVQLADHYQQ NTPIGDGPVLLPDNHYLSHQSALSKDPNEKRDHMVLL EFVTAAGITHGMDELYKSRGPYSIVSPKC |
| 9 | mRuby2 | MVSKGEELIKENMRMKVVMEGSVNGHQFKCTGEGEGN PYMGTQTMRIKVIEGGPLPFAFDILATSFMYGSRTFI KYPKGIPDFFKQSFPEGFTWERVTRYEDGGVVTVMQT SLEDGCLVYHVQVRGVNFPSNGPVMQKKTKGWEPDNT EMMYPADGGLRGYTHMALKVDGGGHLSCSFVTTYRSK KTVGNIKMPGIHAVDHRLERLEESDNEMFVVQREHAV AKFAGLGGGMDELYK |

In another preferred embodiment, the polypeptide according to the present invention comprises an amino acid sequence of GEPII 1.0 (SEQ ID NO:13) or R-GEPII 1.0 (SEQ ID NO: 21).

In another preferred embodiment, the first signaling domain and the second signaling domain comprise post-translational modifications, such as a conjugated fluorescein molecule or other small molecule fluorophores or detectable moieties, which may contribute to generating the detectable signal of the first signaling domain together with the second signaling upon binding of the K⁺ to the potassium sensor.

In another preferred embodiment, the potassium sensor comprises an amino acid sequence of Kbp. In a preferred embodiment, the potassium sensor comprises an amino acid sequence which exhibits at least 75% identity to the sequence according to SEQ ID NO:3. In a preferred embodiment, the potassium sensor comprises an amino acid sequence which exhibits at least 80% identity to the sequence according to SEQ ID NO:3. In a preferred embodiment, the potassium sensor comprises an amino acid sequence which exhibits at least 85% identity to the sequence according to SEQ ID NO:3. In a preferred embodiment, the potassium sensor comprises an amino acid sequence which exhibits at least 90% identity to the sequence according to SEQ ID NO:3. In a preferred embodiment, the potassium sensor comprises an amino acid sequence which exhibits at least 95% identity to the sequence according to SEQ ID NO:3. In a preferred embodiment, the potassium sensor comprises an amino acid sequence which exhibits at least 100% identity to the sequence according to SEQ ID NO:3.

In another preferred embodiment, the amino acid sequence of the polypeptide of the present invention comprises from N-terminus to C-terminus:
i) the first signaling domain;
ii) the potassium sensor, wherein preferably the first domain of the potassium sensor is followed by the second domain of the potassium sensor; and
iii) the second signaling domain.

In another preferred embodiment, the polypeptide according to the present invention may further comprise at least one linker sequence. The linker, which preferably has a flexible, i.e. not rigid, structure, may modify the sensitivity of the detectable signal. The linker amino acid sequence may be located in the amino acid sequence of the polypeptide between any two of the first signaling group, the first domain of the potassium sensor, the second domain of the potassium sensor and the second signaling domain. In a preferred embodiment, the linker amino acid sequence is preceded by the amino acid sequence of the first domain of the potassium sensor and followed by the second domain of the potassium sensor. However, it is of course also possible that the linker domain is located between the potassium sensor and the first signaling domain or between the potassium sensor and the second signaling domain.

In one embodiment, the linker contains the amino acid sequence -GGGG- (SEQ ID NO:22).

In a preferred embodiment, the polypeptide further comprises at least one linker amino acid sequence of formula (I):

$$-(GGS)_x(GGGGS)_y(GG)_z- \quad \text{(I) (SEQ ID NO: 23)}$$

wherein
x is the integer 0 or 1,
y is an integer from 1 to 6,
z is the integer 0 or 1.

In a preferred embodiment, y is not 4.
In one preferred embodiment, y is 2, 3 or 5.
In one preferred embodiment, x is 0, y is 1 and z is 1. It is in this embodiment further preferred that the polypeptide comprises an amino acid sequence of SEQ ID NO:14.

In another preferred embodiment, x is 0, y is 2 or 3, and z is 0. It is in this embodiment further preferred that the polypeptide comprises an amino acid sequence of SEQ ID NO:15 or SEQ ID NO:16.

In yet another preferred embodiment, x is 0, y is 4 and z is 1. It is in this embodiment further preferred that the polypeptide comprises an amino acid sequence of SEQ ID NO: 17.

In another preferred embodiment, x is 1, y is 5 and z is 0. It is in this embodiment further preferred that the polypeptide comprises an amino acid sequence of SEQ ID NO: 18, SEQ ID NO: 19 or SEQ ID NO: 20.

It is known that extracellular K⁺ levels in biological systems typically range from about 1 mM to about 10 mM. In contrast, intracellular cytosolic and organelle K⁺ concentrations typically range from about 100 mM to 300 mM. As will be apparent from the examples, the polypeptides of the present invention may provide different sensitivities for K⁺ and this may dependent on the presence of a linker sequence or amino acid substitutions in SEQ ID NO: 1 and/or SEQ ID NO: 2 as described above. It needs to be understood that the skilled person would thus use a polypeptide according to the present invention with a suitable sensitivity for the respective application. For example, a skilled person might use a polypeptide with a relatively low $EC_{50}$ value, i.e. up to 20 mM, preferably up to 10 mM, and more preferably of about 5 mM, for measuring extracellular $K^+$ levels and polypeptides according to present invention having a higher $EC_{50}$ value, i.e. from about 10 to about 300 mM, preferably from about 50 to about 150 mM for measuring intracellular $K^+$ concentrations. The $EC_{50}$ values here referred to are the $EC_{50}$ values obtained by the method as described in example 4.

Thus, in a preferred embodiment, the polypeptide of the present invention provides an $EC_{50}$ value from about 10 to about 300 mM. This polypeptide may be particularly suitable for the detection of intracellular $K^+$.

In another preferred embodiment, the polypeptide of the present invention provides an $EC_{50}$ value from about up to 20 mM and preferably of about 5 mM for measuring extracellular $K^+$.

In another preferred embodiment, the polypeptide further comprises a targeting sequence. The targeting sequence is an amino acid sequence that directs the polypeptide to a targeted organelle or sub-domain of a cell or extracellular secretion. The targeted organelles and sub-domains may for example include the nucleus, mitochondria, the endoplasmic reticulum (ER), the cell surface, the nuclear envelope and the subplasmalemmal area. The targeting sequence may be located at the N-terminus or the C-terminus of the polypeptide. The addition of a nuclear export sequence, for example the amino acid sequence LPPLERLTL (SEQ ID NO:24) to the C-terminus of the polypeptide, may result in the localization of the polypeptide in the cytosol only. The addition of a C-terminal nuclear leading sequence (KRSWSMAFC) (SEQ ID NO:25) may result in the targeting of the nucleus.

Mitochondria may be targeted by a mitochondrial targeting sequence such as a tandem dimeric repeat of COX8. Examples of an ER targeting sequence include the ER targeting sequence of calreticulin on the N-terminus plus KDEL retention sequence on the C-terminus of the polypeptide of the invention. A GPI-anchor sequence may for example direct the polypeptide to the cell surface. Examples of a perinuclear target sequence include emerin, wherein the sequence of the polypeptide of the present invention is fused to the C-terminus of emerin. An example of a subplasmalemmal area targeting sequence is the CAAX domain of the GTPase Kras isoform b, e.g. having a sequence MSKDVKKKKKSKTKCVIM (SEQ ID NO:26) fused to the C-terminus of the polypeptide according to the present invention.

In a preferred embodiment, the polypeptide of the present invention is an isolated polypeptide.

In another aspect the present invention relates to a polynucleotide encoding the polypeptide according to the present invention.

It will be apparent to the person skilled in the art that due to the degeneracy of the genetic code a given polypeptide according to the invention may be encoded by different nucleotide sequences.

In a preferred embodiment, the polynucleotide according to the invention has a length of less than 9000 nucleotides, less than 8000 nucleotides, less than 7000 nucleotides, less than 6000 nucleotides, less than 5000 nucleotides, less than 4000 nucleotides, less than 3000 nucleotides, less than 2000 nucleotides, less than 1000 nucleotides, or less than 500 nucleotides.

In a further preferred embodiment the isolated polynucleotide according to the invention has a length of between at least 24 and 9000 nucleotides, preferably between at least 24 and 8000 nucleotides, more preferably between at least 24 and 7000 nucleotides, more preferably between at least 24 and 6000 nucleotides, more preferably between at least 24 and 5000 nucleotides, and even more preferably between at least 24 and 4000 nucleotides. In another preferred embodiment the polynucleotide according to the invention has a length of between at least 60 and 9000 nucleotides, preferably between at least 60 and 8000 nucleotides, more preferably between at least 60 and 7000 nucleotides, more preferably between at least 60 and 6000 nucleotides, more preferably between at least 60 and 5000 nucleotides, and even more preferably between at least 60 and 4000 nucleotides. In a further preferred embodiment the polynucleotide according to the invention has a length of between at least 90 and 9000 nucleotides, preferably between at least 90 and 8000 nucleotides, more preferably between at least 90 and 7000 nucleotides, more preferably between at least 90 and 6000 nucleotides, more preferably between at least 90 and 5000 nucleotides, and even more preferably between at least 90 and 4000 nucleotides. In yet another preferred embodiment the polynucleotide according to the invention has a length of between at least 120 and 9000 nucleotides, preferably at least between 120 and 8000 nucleotides, more preferably between at least 120 and 7000 nucleotides, more preferably between at least 120 and 6000 nucleotides, more preferably between at least 120 and 5000 nucleotides, and even more preferably between at least 120 and 4000 nucleotides. In yet another preferred embodiment the isolated polynucleotide according to the invention has a length of between at least 300 and 9000 nucleotides, preferably between at least 300 and 8000 nucleotides, more preferably between at least 300 and 7000 nucleotides, more preferably between at least 300 and 6000 nucleotides, more preferably between at least 300 and 5000 nucleotides, and even more preferably between at least 300 and 4000 nucleotides.

In another preferred embodiment an polynucleotide according to the invention has a length of at least 300 nucleotides, at least 400 nucleotides, at least 1000 nucleotides, at least 2000 nucleotides or at least 2500 nucleotides.

In a preferred embodiment, the polynucleotide according to the invention comprises or consists of a sequence which exhibits at least 80% identity to the sequence according to SEQ ID NO:10. In a further preferred embodiment the polynucleotide according to the invention comprises or consists of a sequence which exhibits at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO:10. In a particularly preferred embodiment the polynucleotide according to the invention comprises or consists of a sequence which exhibits at least 85%, preferably at least 90%, more preferably at least 95% or even more preferably at least 98% identity to the sequence according to SEQ ID NO:10.

In a preferred embodiment, the polynucleotide according to the invention comprises or consists of a sequence which exhibits at least 80% identity to the sequence according to SEQ ID NO:11. In a further preferred embodiment the polynucleotide according to the invention comprises or consists of a sequence which exhibits at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO:11. In a particularly preferred embodiment the polynucleotide according to the invention comprises or consists of a sequence which exhibits at least 85%, preferably at least 90%, more preferably at least 95% or even more preferably at least 98% identity to the sequence according to SEQ ID NO:11.

In a preferred embodiment, the polynucleotide according to the invention comprises or consists of a sequence which exhibits at least 80% identity to the sequence according to SEQ ID NO:12. In a further preferred embodiment the polynucleotide according to the invention comprises or consists of a sequence which exhibits at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO:12. In a particularly preferred embodiment the polynucleotide according to the invention comprises or consists of a sequence which exhibits at least 85%, preferably at least 90%, more preferably at least 95% or even more preferably at least 98% identity to the sequence according to SEQ ID NO:12.

Sequences of SEQ ID NO: 10 to 12 are shown below in Table 4.

TABLE 4

Nucleotide Sequences encoding the BON domain, LysM domain and Kbp

| SEQ ID NO: | Comment | Nucleotide sequence |
|---|---|---|
| 10 | BON | CAGGCGAAGAAGGTGCAGGAGCATCTGAACAAAAC CGGTATACCGGATGCCGATAAAGTGAATATTCAAA TTGCCGACGGCAAAGCGACGGTCACTGGTGACGGC CTGAGTCAGGAGGCGAAGGAGAAAATCCTTGTTGC GGTGGGGAATATTTCCGGTATTGCCAGTGTCGATG ATCAGGTGAAAACG |
| 11 | LysM | CAGTTTTATACCGTTAAGTCTGGCGACACTCTGAG TGCCATTTCCAAACAGGTCTACGGTAACGCTAATC TGTACAATAAAATCTTCGAAGCGAATAAACCGATG CTAAAAAGCCCGGATAAAATTTATCCGGGGCAAGT GTTGCGTATT |
| 12 | Kbp | ATGGGTCTGTTCAATTTTGTGAAAGATGCCGGAGA AAAACTCTGGGACGCGGTTACAGGTCAGCACGATA AAGACGATCAGGCGAAGAAGGTGCAGGAGCATCTG AACAAAACCGGTATACCGGATGCCGATAAAGTGAA TATTCAAATTGCCGACGGCAAAGCGACGGTCACTG GTGACGGCCTGAGTCAGGAGGCGAAGGAGAAAATC CTTGTTGCGGTGGGGAATATTTCCGGTATTGCCAG TGTCGATGATCAGGTGAAAACGGCGACACCAGCCA CTGCCCAGCCAGTTTTATACCGTTAAGTCTGGCGAC ACTCTGAGTGCCATTTCCAAACAGGTCTACGGTAA CGCTAATCTGTACAATAAAATCTTCGAAGCGAATA AACCGATGCTAAAAAGCCCGGATAAAATTTATCCG GGGCAAGTGTTGCGTATTCCGGAAGAG |

A polynucleotide according to the invention may be a single or double stranded RNA or DNA molecule.

In some embodiments the isolated polynucleotide according to the invention may be inserted into a vector such as an expression vector. The expression vector may e.g. be a prokaryotic or eukaryotic expression vector such as e.g. an isolated plasmid, a minichromosome, a cosmid, a bacterial phage, a retroviral vector or any other vector known to the person skilled in the art. The person skilled in the art will be familiar with how to select an appropriate vector according to the specific need. In a preferred embodiment, the expression vector is an isolated plasmid.

The present invention thus also relates to an expression vector comprising a polynucleotide according to the invention.

In one aspect, the present invention relates to a cell comprising the polypeptide, the polynucleotide, expression vector and/or plasmid encoding the polypeptide of the present invention. Said cell is not a human embryonic stem cell. Examples of cells include but are not limited to, in vitro cell culture cells or cell lysates of eukaryotic cells, such as mammalian cells, human cells or plant cells or prokaryotic cells each of which optionally may have been genetically modified by methods commonly known to the person skilled in the art such as transfecting or transforming of said cells.

In one aspect, the prevent invention relates to a method for detecting positively charged potassium ions in a sample, comprising the steps of
  a) providing a polypeptide according to the present invention;
  b) contacting the polypeptide according to the present invention;
  c) measuring the signal generated by the first signaling domain;
wherein a change in signal intensity after contact with the sample indicates the presence of the potassium ions in the sample.

In one aspect, the prevent invention relates to a method for detecting positively charged potassium ions in a sample, comprising the steps of
  a) providing a polypeptide according to the present invention;
  b) contacting the polypeptide according to the present invention;
  c) measuring the signal generated by the first signaling domain; and/or
  d) measuring the signal generated together by the first signaling domain and the second signaling domain;
wherein a change in signal intensity after contact with the sample indicates the presence of the potassium ions in the sample.

The step a) of providing the polypeptide occurs outside of the human body.

In one embodiment of said method, the change in signal intensity after contact with the sample compared to the signal of the polypeptide in the absence of the sample indicates the presence of $K^+$ in the sample.

In another preferred embodiment, the method according to the present invention is a (quantitative) in vivo imaging method.

In a preferred embodiment, the measured signal is a fluorescence signal, a colorimetric signal or a FRET signal. Preferably, the signal may be generated upon binding of $K^+$ to the potassium sensor of the polypeptide according to the present invention. In a preferred embodiment, the signal may be generated by a FRET-donor-acceptor pair, split-enzyme pair or split-fluorescent protein pair. The detection may occur by methods commonly known to the person skilled in the art.

In one embodiment, the measured signal is a fluorescence signal. In a preferred embodiment, the fluorescence signal is quenched by binding of $K^+$ to the potassium sensor domain.

In a more preferred embodiment, the measured detectable signal is a FRET signal. Preferably, the FRET signal is generated by the first signaling domain and the second signaling domain. More preferably, the FRET signal is generated by a FRET-donor-acceptor pair, preferably YFP, such as CPV, and CFP. The person skilled in the art is aware how to measure FRET signals. Preferably, the FRET between YFP and CFP is measured after excitation with light at a wavelength in the range of from about 420 nm to about 450 nm. More preferably, the measurement is performed after excitation with light at about 440 nm. It is also preferred that the emission of light is measured at a wavelength in the range from about 525 nm to about 545 nm and more preferably about 535 nm.

In another preferred embodiment, the FRET pair is Clover and mRuby2 instead of YFP and CFP. In this case, the FRET signal is measured after excitation with 470 nm to about 490 nm and/or an emission of light in the range of from about 510 nm to 520 nm (Emission 1) and 590 nm to about 610 nm (Emission 2).

In a preferred embodiment, the step a) of the method for detecting $K^+$, i.e. the providing a polypeptide according to the invention, may comprise transfecting at least one cell outside the human or animal body or transforming a prokaryotic cell with a polynucleotide, a plasmid and/or an expression vector encoding the polypeptide according to the present invention. The polypeptide according to the invention may then be provided by protein synthesis of said cell. The polypeptide according to the present invention may then either be isolated from the cell, secreted by the cell or remain inside the cell. In another preferred embodiment, the polypeptide according to the present invention may be provided in step a) of the method according the present by providing a cell according to the present invention.

In a preferred embodiment, the method according to the present invention may detect the presence of potassium ions in any kind of sample. More preferably, the sample is selected from the group consisting of biological samples or liquid samples or a combination thereof. Even more preferably, the sample is a cell culture, a cell pellet, a cell lysate, a tissue sample from a human or an animal, blood, or a liquid containing $K^+$. In one embodiment, the sample may also comprise a biological sample, such as a cell culture, including the monolayer culture of cells or a 3-dimensional cell culture, a cell suspension, a cell pellet, a cell lysate, a tissue sample from a human or an animal and a liquid sample containing $K^+$. Preferably, the method according to the present invention may then be used to characterize the influence of $K^+$ on the biological sample by detecting the presence and/or distribution of $K^+$ and optionally in combination with determining other relevant parameters of the biological sample, such as cell apoptosis, cell signaling, cell gene expression or the like.

In one aspect, the polypeptide of the present invention may thus be used for detecting $K^+$ in a sample as described above. In a preferred embodiment, the use according to the present invention comprises the use of the polypeptide according to the present invention in (quantitative) in vivo imaging. The term in "vivo imaging" refers to the imaging in living cells outside the human body such as microscopy of isolated living cells that were cultured in vitro. The intracellular polypeptide according to the present invention may for example indicate changes in $K^+$ levels in the cytosol, subplasmalemmal area, nucleus, endoplasmic reticulum, nuclear envelop and mitochondria e.g. in response to defined stimuli or stresses.

In another preferred embodiment, the isolated polypeptide of the invention may be contacted in a suitable vessel, e.g. a multi-well plate, with a biological sample and the potassium concentration may be directly measured, e.g. using a plate fluorescence reader. It is one advantage of the use of the polypeptide according to the present invention that such an assay would require a low amount of sample (only about 5-10 µl) compared to the amount of the biological sample needed for measuring the potassium concentration using electrodes, which typically requires approximately 100 to 1000 µl or even more volume to adequately bath the $K^+$ electrode. Therefore, the determination of the serum $K^+$ concentration by using such a $K^+$ electrode of small laboratory animals such as mice, which have a total blood volume of 1.5-2.5 ml (6-8% of the bodyweight), usually requires the sacrifice of the animal for maximal blood concentration.

In another preferred embodiment, the polypeptide according to the present invention may be used in an in vitro cell death assay. Virtually in all cell types, particularly in excitable cells, tremendous energy is required to maintain a $Na^+$ and $K^+$ gradient across the plasma membrane via the $Na^+$/$K^+$-ATPase. Under stress conditions, not enough energy becomes available for the cells and they will accordingly have a reduced viability and will eventually undergo cell death. In this embodiment of the present invention, isolated polypeptide according to the present invention is added to the culture medium of cultivated cells and may be used to monitor the $K^+$ concentration in the culture medium over time. When the viability of the cells decreases or the occurrence of cell death increases, the $K^+$ concentration in the medium will increase. This can then be detected by using the polypeptide of the present invention, accordingly. The use of the polypeptide according to the present invention in this assay provides the advantage that it allows for real-time measurements that do not further harm/influence the cells in contrast to other state of the art cell death/viability assays (e.g. MTT assay or resazurin-based assays such as the CellTiter-Blue® Cell Viability assay).

In another embodiment, the polypeptide according to the present invention is used in a cell growth assay. It is known that the concentration of $K^+$ decreases when cells are growing. When the isolated polypeptide according to the present invention is added to the culture medium of cultured cells, it is possible to again monitor the extend of cell growth. This assay may for example be used to differentiate between a growing bacterial cell culture and a bacterial cell culture containing mostly dead cells that do not grow and replicate. This cannot be determined by current standard methods to monitor bacterial growth, e.g. by measuring the optical density (OD600) of the bacterial cell culture.

In yet another embodiment, the polypeptide according to the present invention may be used as a sensor for the visualization of extracellular $K^+$ fluctuations in living animals using intravital microscopy, e.g. of the brain or muscle, in real time. The polypeptide according to the present invention may in this application for example be topically applied to the animals. In this context, the polypeptide according to the present invention may e.g. be used as a research tool for the investigation of cancer or neurological disorders such as epilepsy, migraine or craniocerebral trauma for the study of animal models.

In one aspect, the present invention also relates to a kit for detecting K⁺ in a sample comprising at least one of:
  a) a polypeptide according to the invention;
  b) a polynucleotide according to the invention or the vector according to the invention; and/or
  c) a cell according to the invention.

Examples of such kits include kits for determining cell death or cell viability as described above. Beside the polypeptide of the present invention, such a kit may for example include at least one of the following items:
  a) a suitable K⁺-free buffer for diluting the sample;
  b) at least one standard solution with a known K⁺ concentration as a positive control;
  c) if the kit contains more than one solution, the standard solutions may contain different concentrations of K⁺ for obtaining a calibration curve using said standard solutions; or
  d) a suitable buffer for diluting the polypeptide according to the present invention.

A kit comprising the polynucleotide or the vector according to the present invention may further comprise plasmids encoding only one or both signaling domains or only the potassium sensor for generating control samples. The kit may further comprise a suitable buffer for diluting the polynucleotide or the vector.

A kit comprising the cell according to the present invention may further comprise a suitable culture medium and/or cryopreservation medium for the cell.

In yet another embodiment, the polypeptide according to the present invention may also be used in a portable K⁺ quick test kit. The polypeptide according to the present invention may in such a test be present in a solution, preferably a potassium free solution, or it can be immobilized on a solid phase or beads.

Definitions

The following definitions are introduced. As used in this specification and in the intended claims, the singular forms of "a" and "an" also include the respective plurals unless the context clearly dictates otherwise.

It is to be understood that the term "comprise", and variations such as "comprises" and "comprising" is not limiting. For the purpose of the present invention the term "consisting of" is considered to be a preferred embodiment of the term "comprising".

If hereinafter a group is defined to comprise at least a certain number of embodiments, this is meant to also encompass a group which preferably consists of these embodiments only.

The terms "about" and "approximately" or "substantially the same" in the context of the present invention denote an interval of accuracy that a person skilled in the art will understand to still ensure the technical effect of the feature in question. The term typically encompasses a deviation from the indicated numerical value of ±10% and preferably of ±5%.

As used herein, the term "domain" refers to building blocks of polypeptides or fusion proteins. The term domain thus comprises parts of a polypeptide that can fold, function and/or exist independently of the rest of the polypeptide chain or structure. For example, cyan fluorescent protein is considered as a domain when it is a part of a fusion protein. Further, the term domain, as used herein, also comprises each part of a split-enzyme or split fluorescent protein, wherein each part is considered as a domain even though the two domains of a split enzyme or split fluorescent protein may only fold and function together.

As used herein, the term "polypeptide" and "protein" are used interchangeably herein to describe protein molecules that may comprise either partial or full-length proteins. The term includes "fusion proteins", comprising proteins or polypeptides that have an amino acid sequence derived from two or more proteins. The fusion protein may also include linking regions of amino acids between amino acid portions derived from separate proteins.

As used herein, the term "detectable signal" refers to an increase or decrease of signals commonly used in technical fields of biochemistry, chemistry, medical or diagnostic technology. Examples of the detectable signal include, but is not limited to, an electrical (e.g., capacitance), mechanical, optical, acoustic or thermal signal. Preferably, the optical signal may be a fluorescence signal, a FRET signal, a colorimetric signal or an electrochemiluminescence signal. It is also preferred that the signal may be detectable, i.e. the signal and a respective change of the signal may be monitored using the appropriate technological equipment. Preferably, the detectable signal may be a signal generated or altered in a proximity-dependent manner, for example induced by a conformational change of a polypeptide.

The term "FRET" as used herein refers to fluorescence resonance energy transfer between or within molecules. In FRET methods, one fluorophore is able to act as an energy donor and one other is an energy acceptor. These are sometimes known as a reporter and a quencher, respectively. The donor may be excited with a specific wavelength of light for which it will normally exhibit a fluorescence emission wavelength. The acceptor may also be excited at a wavelength such that it can accept the emission energy of the donor molecule by a variety of distance-dependent energy transfer mechanisms. Generally, the acceptor accepts the emission energy of the donor when they are in close proximity. The donor and the acceptor may be different molecules or may be separate parts of the same molecule, such as two different domains of a polypeptide. FRET measuring techniques are well known in the art.

As used herein, the term "FRET-donor-acceptor pair" refers to fluorophores representing the energy donor and the energy acceptor capable of FRET as described above. In this context, the term "fluorophore" refers to a component of a molecule that causes a molecule to be fluorescent. It is a functional group in a molecule which will absorb light of a specific wavelength and re-emit light at a different (but equally specific) wavelength. The amount and wavelength of the emitted light depend on both the fluorophore and the chemical environment of the fluorophore. Fluorophores include, but are not limited to, fluorescein isothiocyanate (FITC), a reactive derivative of fluorescein, rhodamine (TRITC), coumarin, cyanin dyes (Cy) e.g. Cyanine 3, Cyanine 5 or Cyanine 7, fluorescent proteins such as the green fluorescent protein (GFP) from *Aequorea Victoria* or *Renilla reniformis* or proteins variants thereof such as yellow fluorescent protein (YFP) including Citrine, Venus, and Y pet; blue fluorescent protein (BFP) such as EBFP, EBFP2, Azurite, mKalamal; cyan fluorescent protein (CFP) such as ECFP, Cerulean, CyPet; and other florescent proteins such as UnaG, dsRed, mRuby2, Clover, eqFP611, Dronpa, TagRFPs, KFP, EosFP, Dendra, IrisFP, Clover, mRubby, mKOk and mKO2. Small molecule fluorophores such as fluorescein isothiocyanate (FITC), a reactive derivative of fluorescein, rhodamine (TRITC), coumarin, cyanin (Cy), may be conjugated to proteins and act as a fluorophore. Examples of fluorophores that may be used as a FRET-donor-acceptor pair include, but are not limited to, CFP as donor and YFP as acceptor, EGFP as donor and Cy3 as acceptor, or EGFP as donor and YFP as acceptor, or Clover as Donor and mRuby2 as acceptor or cpEGFP as donor and mKO2 as acceptor.

As used herein, the term "split enzyme" refers to a biologically active enzyme that is split into at least two portions that have at least reduced or no biologically activity. In this context, the term "split enzyme pair" refers to the at least two at least partially inactive enzyme portions. Upon close proximity, the enzyme portions interact to form the biologically active enzyme, which can be detected using conventional enzyme detection techniques. The split enzyme technology is also further described in WO 2005/094441 A2. Examples of split enzymes include, but are not limited to, *Renilla* luciferase that can be reconstituted and monitored via bioluminescence; complementing split β-galactosidase wherein the activity can be monitored via colorometric, chemiluminescence, or fluorescence detection; split β-lactamase whose complementation may be assayed by the color change of nitrocefin upon hydrolysis or by fluorescence via CCF-2/AM; GTPases (change of charge), peroxidases (colorometric), nucleases (endo and exo cleavage), restriction endonucleases (sequence specific endo cleavage), proteases (protein cleavage), ligases (ligating nucleic acid oligos), and thiol-disulfide oxidoreductases (conformational change through disulfide bonds).

As used herein, the term "split fluorescent protein (SFP) pairs" refers to at least two portions of a fluorescent protein. SFPs are composed of multiple peptide or polypeptide fragments that individually are not fluorescent, but, when complemented, form a functional fluorescent molecule. For example, Split-Green Fluorescent Protein (Split-GFP) is an SFP. Some engineered Split-GFP molecules are self-assembling. (See, e.g., U.S. Pat. App. Pub. No. 2005/0221343 and PCT Pub. No. WO/2005/074436; Cabantous et al., Nat. Biotechnol., 23:102-107, 2005; Cabantous and Waldo, Nat. Methods, 3:845-854, 2006). US2012282643 also describes Split-Yellow Fluorescent Protein variants and Split-Cyan Fluorescent Protein variants.

The determination of "percent identity" between two sequences as used herein is preferably accomplished using the mathematical algorithm of Karlin and Altschul (1993) Proc. Natl. Acad. Sci USA 90: 5873-5877. Such an algorithm is e.g. incorporated into the BLASTn and BLASTp programs of Altschul et al. (1990) J. Mol. Biol. 215: 403-410 available at NCBI (http://www.ncbi.nlm.nih.gov/blast/Blast.cgi).

The determination of percent identity is preferably performed with the standard parameters of the BLASTn and BLASTp programs.

BLAST polynucleotide searches are preferably performed with the BLASTn program.

For the general parameters, the "Max Target Sequences" box may be set to 100, the "Short queries" box may be ticked, the "Expect threshold" box may be set to 10 and the "Word Size" box may be set to 28. For the scoring parameters the "Match/mismatch Scores" may be set to 1,−2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "Mask lower case letters" box may not be ticked.

BLAST protein searches are preferably performed with the BLASTp program.

For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

The percent identity is determined over the entire length of the respective reference sequence, i.e. over the entire length of the sequence according to the SEQ ID NO or SEQ ID NOs recited in the respective context. For example, an amino acid sequence which exhibits at least 80% identity to the sequence according to SEQ ID NO:1 exhibits at least 80% identity to SEQ ID NO:1 over the entire length of SEQ ID NO:1. In another example, a sequence which exhibits at least 80% identity to the sequence according to SEQ ID NO:3 exhibits at least 80% identity to SEQ ID NO:3 over the entire length of SEQ ID NO:3.

The term "isolated" in the context of the present invention indicates that a polypeptide or polynucleotide has been removed from its natural environment and/or is presented in a form in which it is not found in nature. An "isolated" polypeptide or an "isolated" polynucleotide may also be a polypeptide or polynucleotide that has been generated in vitro.

As used herein, the term "amino acid substitution" refers to a substitution in an amino acid sequence according to a conservative or a non-conservative substitution, preferably a conservative substitution. In some embodiments, a substitution also includes the exchange of a naturally occurring amino acid with a non-natural amino acid. A conservative substitution comprises the substitution of an amino acid with another amino acid having a chemical property similar to the amino acid that is substituted. Preferably, the conservative substitution is a substitution selected from the group consisting of:

(i) a substitution of a basic amino acid with another, different basic amino acid;
(ii) a substitution of an acidic amino acid with another, different acidic amino acid;
(iii) a substitution of an aromatic amino acid with another, different aromatic amino acid;
(iv) a substitution of a non-polar, aliphatic amino acid with another, different non-polar, aliphatic amino acid; and
(v) a substitution of a polar, uncharged amino acid with another, different polar, uncharged amino acid.

A basic amino acid is preferably selected from the group consisting of arginine, histidine, and lysine. An acidic amino acid is preferably aspartate or glutamate.

An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of an amino acid with any amino acid that does not fall under the above-outlined conservative substitutions (i) through (v).

As used herein, the term "biological sample" refers to a sample of tissue (e.g., tissue biopsy), organ, cell, cell lysate, or body fluid (blood, urine, saliva, bile, serum, cerebrospinal fluid and the like) outside the body of a human or an animal.

Further the term "biological sample" also includes in vitro cell cultured cells or cell lysates of eukaryotic cells, such as mammalian cells, human cells or plant cells or prokaryotic cells which optionally may have been genetically modified by methods commonly known to the person skilled in the art, including methods of transfecting and transforming.

As used herein, the term "binding" refers to an attractive interaction between two molecules that results in a stable association in which the molecules are in close proximity to each other. The result of binding is sometimes the formation of a molecular complex in which the attractive forces holding the components together are generally non-covalent, and thus are normally energetically weaker than covalent bonds.

EXAMPLES

1. Cell Culture, Cell Transfection, Chemicals and Buffers

HeLa cells were grown in Dulbeccos's Modified Eagle Medium (DMEM, Sigma Aldrich) containing 10% fetal bovine serum, 100 U/ml penicillin and 100 µg/ml streptomycin. At 60-80% confluence, cells in 30-mm imaging dishes were transfected with 1 ml of serum- and antibiotic-free medium that had been mixed with 1.5 µg of the appropriate plasmid DNA and 3 µg TransFast™ transfection reagent (Promega). Cells were maintained in a humidified incubator (37° C., 5% CO2, 95% air) for 16-20 hours prior to changing back to the respective culture medium. All experiments were performed 24 hours after transfection. Valinomycin was purchased from Sigma Aldrich and used in a final concentration of 7 µM. The experimental buffer used was composed of (in g/L): 8.0 or 7.6 NaCl, 1.44 $Na_2HPO_4$, 0.12 $NaH_2PO_4$, pH 7.40 using NaOH either with 0.4 KCl or without KCl.

2. Live-Cell Imaging

Fluorescence imaging was performed using the TiLL iMIC (Till Photonics, Graefelfing, Germany), a digital wide field fluorescence imaging system. The red shifted FRET-based R-GEPII was excited at 480 nm and emissions were captured at 510-540 nm (Clover i.e. FRET donor) and 560-610 nm (FRET of Clover to mRuby2), respectively. The CFP/YFP-based GEPII 1.0 (SEQ ID NO: 13) was excited at 430 nm and emissions were recorded at 480 nm and 535 nm, respectively. Data acquisition and control of the digital fluorescence microscope was done using the live acquisition software version 2.0.0.12 (Till Photonics).

3. In Silico Modelling

Models of the BON domain and the full length Kbp were predicted using the online tool Phyre2 (Protein Homology/analogy Recognition Engine V 2.0; http://www.sbg.bio.ic.ac.uk/phyre2/html/page.cgi?id=index). Further analyses of the predicted three dimensional structures of the chimera were performed using the software PyMol viewer, Tunnel prediction was performed using the online tool PoreWalker 1.0 (http://www.ebi.ac.uk/thorntonsrv/software/Pore-Walker/).

4. Detection of $K^+$ by FRET

Figure 2:
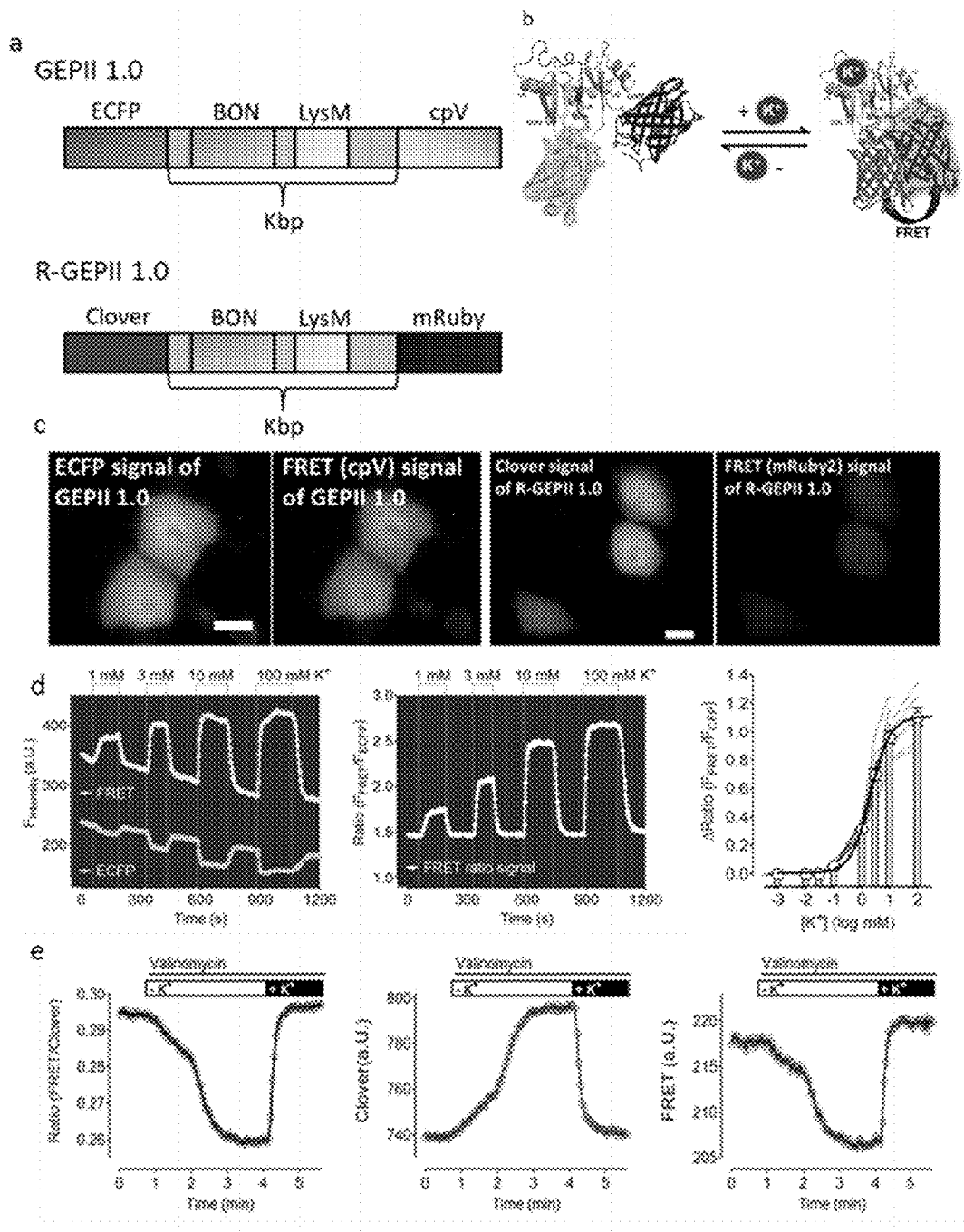
FIG. 2 shows FRET-based polypeptides according to the present invention, in particular (a) a schematic overview of two polypeptides called GEPII 1.0 (SEQ ID NO: 13) and R-GEPII 1.0 (SEQ ID NO: 21), (b) the predicted 3-D structure of R-GEPII 1.0 (SEQ ID NO: 21), (c) HeLa cells expressing either GEPII 1.0 (SEQ ID NO: 13) (the two left panels) or R-GEPII 1.0 (SEQ ID NO: 21) (the two right panels). Scale bar represents 10 µm, (d) ECFP, FRET signals (the left panel), and FRET ratio signals (middle panel) of GEPII 1.0 (SEQ ID NO: 13) over time upon the addition and removal of different K+ concentrations. The right panel shows the concentration response curve of GEPII 1.0 (SEQ ID NO: 13) in permeabilized (3 µM digitonin+2 µM valinomycin) HeLa cells; EC50=2.04 (1.716 to 2.413) mM; N=10. (e) Representative FRET ratio—(left panel), Clover— (middle panel) and FRET signals (right panel) of R-GEPII 1.0 (SEQ ID NO: 21) over time in valinomycin (10 µM) treated HeLa cells.

Plasmid DNA coding for GEPII 1.0 and R-GEPII 1.0 polypeptides (SEQ ID NOs: 13 and 21, respectively) (FIGS. 2a and b) was generated using classical cloning strategies. GEPII 1.0 (SEQ ID NO: 13) comprises an optimized CFP/YFP (sECFP as the FRET donor and cpV as the FRET acceptor) FRET pair (FIG. 2a, upper panel). The red-shifted R-GEPII 1.0 (SEQ ID NO: 21) contains Clover and mRuby2 (FIG. 2a, lower panel and b), which are bright green and red FP variants, respectively, optimized for the generation of bathochromic FRET-based probes with improved dynamics.

Both probes were tested in HeLa cells that either expressed CFP/YFP-based GEPII 1.0 (SEQ ID NO: 13) (FIG. 2c, left panels) or the red-shifted R-GEPII 1.0 (SEQ ID NO: 21) (FIG. 2c, right panels) after transfection of the respective plasmid DNA. In order to control the cytosolic $K^+$ concentration ($[K^+]_{cyto}$), cells were permeabilized with a mixture of digitonin and the $K^+$ ionophore valinomycin (FIG. 2d) or with valinomycin alone (FIG. 2e). Indeed, the FRET ratio signals of GEPIIs increased in response to $K^+$ addition in a concentration dependent manner (FIG. 2d), while FRET fluorescence immediately decreased upon the removal of $K^+$ (FIGS. 2d and e). These experiments confirmed that the design and generation of FP and kbp-based chimeric construct yield functional FRET-based probes that provide a real-time read-out of $K^+$ changes.

In situ, the half maximal effective concentration ($EC_{50}$) of the CFP/YFP based GEPII 1.0 (SEQ ID NO: 13) and the respective R-GEPII 1.0 (SEQ ID NO: 21) was found to be 2.04 (1.72-2.41) mM (FIG. 2d, right panel) and 4.11 (3.25-5.19) mM (n=8), respectively. In order to determine the $EC_{50}$ values in situ (cultured single HeLa cells), cells expressing the GEPIIs were permeabilized with 5 µM digitonin for 10 minutes in a $K^+$ free solution. Digitonin was applied to cells on the microscope using a semi-automatic perfusion system. Continuous FRET ratio imaging over time was used to investigate the $K^+$ sensitivity of the probes. Different $K^+$ concentrations ranging from 0.01 mM to 100 mM were added via the perfusion system until the FRET ratio signal increased and remained stable. The maximal delta FRET ratio values were plotted against the respective logarithmic $K^+$ concentrations and fitted using a sigmoidal concentration response equation. Data analysis was performed using GraphPad Prism 5 software.

5. Rational Design of Polypeptide Variants

In order to manipulate the $K^+$ sensitivity of GEPIIs, we rationally redesigned the wild-type kbp based on sequence analysis and homology 3D-modelling using Phyre-2 and PyMol software. Our predictions as well as preliminary data indicated that mutations that code for charged and polar amino acids in the BON and LysM domain significantly reduce the $K^+$ sensitivity of respective FRET-based GEPIIs.

Figure 3:
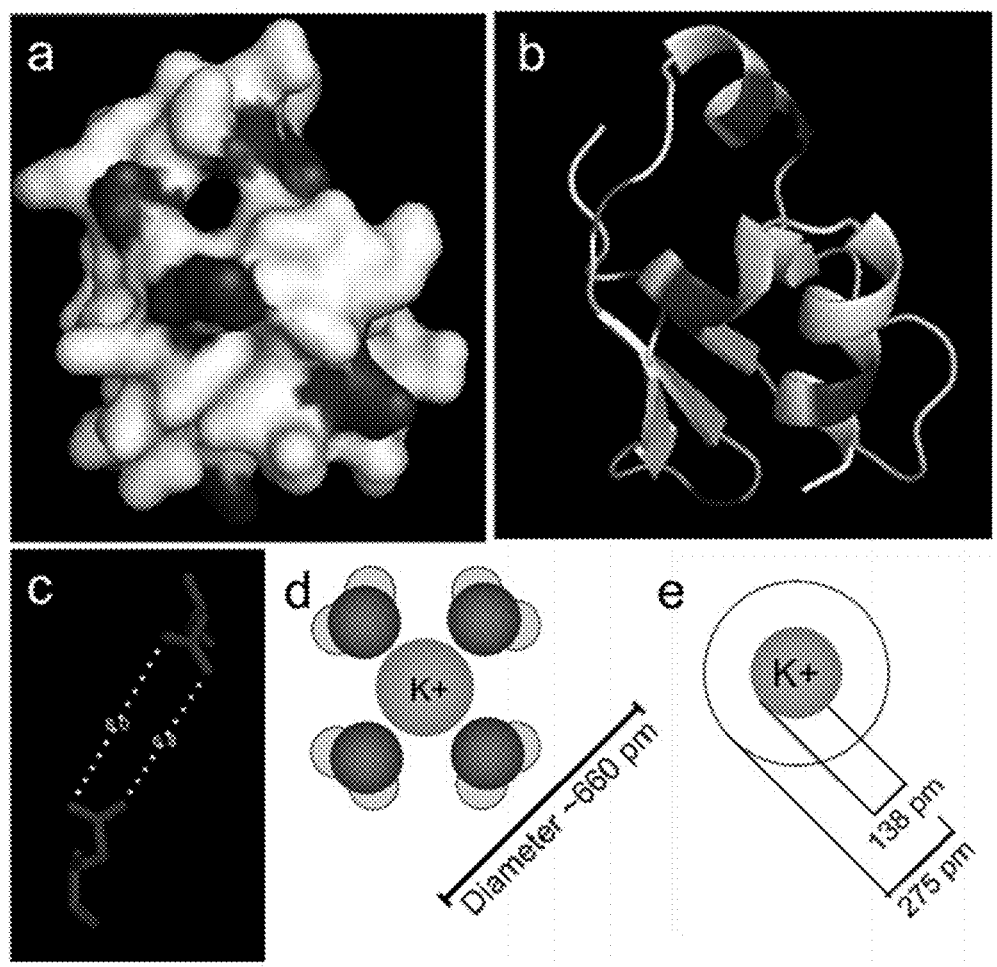
FIG. 3 illustrates the predicted 3-D structure of the $K^+$-binding BON domain (a, b), wherein the acidic amino acids are highlighted. Under (c)

In the wild-type $K^+$-binding BON domain of kbp, 8 positions of acidic amino acids can be identified: D41, D43, D51, D59, E64, E67, D83, and D84 (FIGS. 3a and b, red areas). Interestingly, 3-D modelling of the BON domain using Phyre2 and PyMol predicted a pore or tunnel-like structure (FIG. 3a). The minimal distance of two acidic amino acids within this pore is around 680 to 800 pm (FIG. 3c). Considering a minimal pore diameter of around 660 pm (FIG. 3d). The acidic amino acids close to the pore and within it might well interfere and bind a hydrated $K^+$ ion (FIG. 3e).

Moreover, sequence analyses combined with 3-D modeling of the BON domain (FIG. 3) predicted that in addition to all the acidic amino acids Q (glutamine) at 27, N (asparagine) at 35, N (asparagine) at 75, and G (glycine) at 53 are considered to be important for $K^+$ sensing.

Three negatively charged amino acids in positions 105 (D), 126 (E) and 408 (D) within the LysM domain, which is supposed to interact with the $K^+$ binding BON domain, also appear to be significant for the conformational change of the protein upon $K^+$ binding.

6. FRET-Detection Using Polypeptide Variants

Plasmid DNA encoding mutants of GEPII 1.0 (SEQ ID NO: 13) were generated using site-directed mutagenesis. Here, primers containing designed single nucleotide polymorphisms were used for respective PCR using herculase II polymerase (Agilent Technologies, Santa Clara, USA). Respective PCR products were then sub-cloned into a pcDNA3.1(−) mammalian expression vector using respective restriction enzymes. Hela cells were then transfected with the respective plasmid DNA and the $EC_{50}$ was determined as describe above in example 4. The results for the respective polypeptide variants are summarized in Table 5.

TABLE 5 sensitivity of GEPII 1.0 variants ("GEPII 1.0" disclosed as SEQ ID NO: 13) with amino acid substitutions

| Construct | Variation in potassium sensor sequence of polypeptide (SEQ ID NO) | $EC_{50}$ in situ (mM) |
|---|---|---|
| GEPII 1.0 (13) | wild-type (wt) Kbp (SEQ ID NO: 3) | 2.6 |
| ΔBON GEPII 1.1 | Q26R, N35Q, N75Q, G52D (SEQ ID NO: 5) | 52.9 |
| ΔLysM GEPII 1.0 ("GEPII 1.0" SEQ ID NO: 13) | D104N, E125Q, D135N (SEQ ID NO: 4) | 55.8 |

7. FRET Detection of Polypeptide Variants Using Different Linker Molecules Between the First Domain of the Potassium Sensor and the Second Domain of the Potassium Sensor Plasmids encoding polypeptides according to the present invention comprising a linker sequence comprising glycine and serine residues were generated using designed forward and reversed primer pairs that encode for the amino acids forming the respective linkers. The forward primer was designed to elongate the wild-type LysM domain with a 5' overhang forming the linker by an overhang extension PCR. The reversed primer was designed to bind the wild-type BON domain and form the same linker at the 3' end. These two PCR products were then fused by an additional PCR and sub-cloned into a pcDNA3.1(−) vector flanked by nucleotide sequences coding for mseCFP and cpV, respectively. The final constructs code for the novel CFP/YFP FRET-based GEPII variants with flexible linkers between the BON and LysM domains of Kbp.

Cells were then transfected with the plasmid DNA and the $EC_{50}$ was determined as described above in example 4. The results for the respective polypeptide variants are summarized in Table 6.

TABLE 6

Sensitivity of GEPII 1.0 variants ("GEPII 1.0" disclosed as SEQ ID NO: 13) wherein BON and LysM are linked by different linker sequences

| Construct | Potassium sensor sequence of polypeptide (SEQ ID NO) | $EC_{50}$ in situ (mM) |
|---|---|---|
| GEPII 1.0 (SEQ ID NO: 13) | wild-type (wt) Kbp (SEQ ID NO: 3) | 2.6 |
| GEPII 2.7 | wtBON-GGGGSGG-wtLysM (SEQ ID NO: 14) | 9.15 |
| GEPII 2.10 | wtBON-GGGGSGGGGS-wtLysM (SEQ ID NO: 15) | 11.54 |
| GEPII 2.15 | wtBON-GGGGSGGGGSGGGGS-wtLysM (SEQ ID NO: 16) | 16.96 |
| GEPII 2.22 | wtBON-GGGGSGGGGSGGGGSGGGGSGG-wtLysM (SEQ ID NO: 17) | 59.95 |

TABLE 6-continued

Sensitivity of GEPII 1.0 variants ("GEPII 1.0" disclosed as SEQ ID NO: 13) wherein BON and LysM are linked by different linker sequences

| Construct | Potassium sensor sequence of polypeptide (SEQ ID NO) | $EC_{50}$ in situ (mM) |
|---|---|---|
| GEPII 2.28 | wtBON-GGSGGGGSGGGGSGGGGSGGGGSGGGGS-wtLysM (SEQ ID NO: 18) | 31.35 |

The polypeptides comprising a linker molecule showed an increased $EC_{50}$ compared to GEPII 1.0 (SEQ ID NO: 13).

8. FRET Detection of Polypeptide Variants Comprising a Linker Between BON and LysM Domains Plasmids encoding polypeptides according to the present invention comprising amino acid substitutions and a linker sequence were generated by using designed forward and reversed primer pairs that encode for the amino acids forming the respective linkers. The forward primer was designed to elongate the ΔLysM domain (see ΔLysM GEPII 1.0 (SEQ ID NO:4) with a 5' overhang forming the linker by an overhang extension PCR. The reversed primer was designed to bind the wild-type BON domain and form the same linker at the 3' end. These two PCR product were then fused by and additional PCR and sub cloned into a pcDNA3.1(−) vector flanked by nucleotide sequences coding for mseCFP and cpV, respectively. The final construct code for the novel CFP/YFP FRET-based GEPII variants with flexible linkers between the BON and ΔLysM domain.

Hela cells were then transfected with the plasmid DNA and the $EC_{50}$ was determined as described above in example 4. The results for the respective polypeptide variants are summarized in Table 7:

TABLE 7 sensitivities of GEP 11 1.0 variants comprising amino acid substitutions and linker sequences

| Construct | Potassium sensor sequence of polypeptide (SEQ ID NO) | $EC_{50}$ in situ (mM) |
|---|---|---|
| ΔLysM GEPII 2.4 | wtBON-GGGG-ΔLysM$^{D104N, E125Q, D135N}$ (SEQ ID NO: 19) | >60 |
| ΔLysM GEPII 2.7 | wtBON-GGGGSGG-ΔLysM$^{D104N, E125Q, D135N}$ (SEQ ID NO: 20) | >100 |

9. Targeting Organelles and Sub-Domains of Cells Expressing the Polypeptide of the Present Invention A big advantage of genetically encoded probes is that they can be precisely targeted to organelles and sub-domains of a cell. Accordingly, the targeting of GEPIIs will enable quantification of $K^+$ levels and dynamics with high spatial and temporal resolution. Due to the lack of targetable $K^+$ probes our current idea of subcellular $K^+$ fluxes is very vague.

Figure 4:
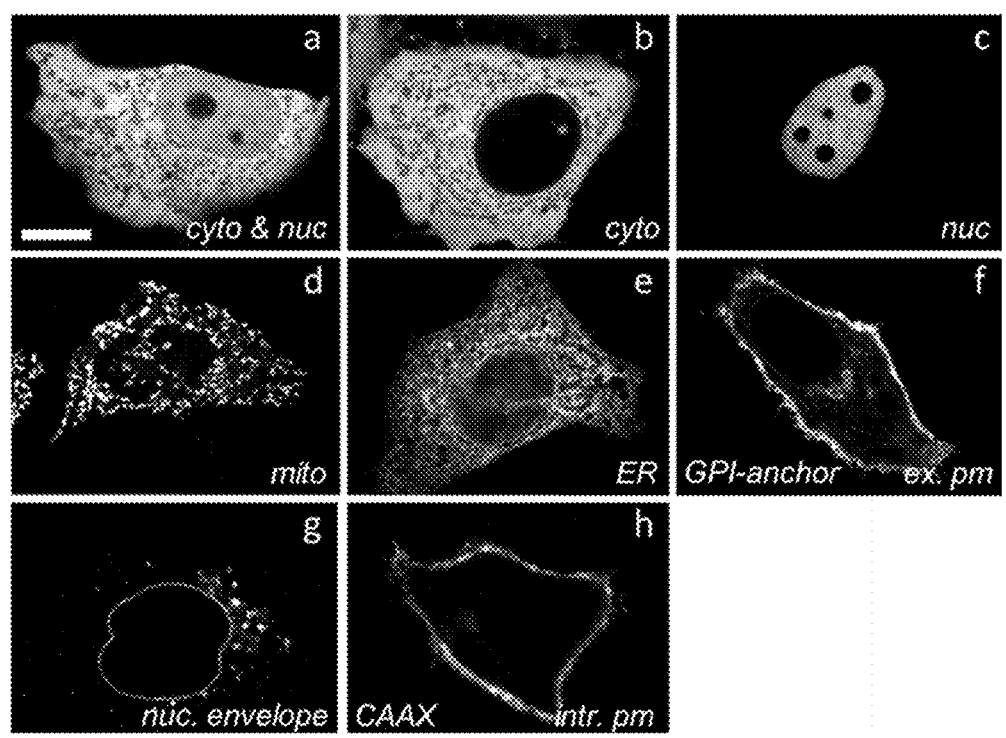
FIG. 4 shows confocal images of GEPII 1.0 variants ("GEPII 1.0" disclosed as SEQ ID NO: 13) expressed in HeLa cells without and with different targeting sequences, the scale bar in panel a represents 10 µm: (a) shows GEPII 1.0 (SEQ ID NO: 13) without any targeting sequence, (b) GEPII 1.0 (SEQ ID NO: 13) with a nuclear export sequence, NES, (c) GEPII 1.0 (SEQ ID NO: 13) with nuclear leading sequence, NLS, (d) GEPII 1.0 (SEQ ID NO: 13) with mitochondrial targeting sequence (tandem dimeric repeat of COX8), (e) GEPII with ER targeting sequence (from calreticulin on the N terminus) plus KDEL retention sequence on the C-terminus, (f) GPI-anchored GEPII 1.0 (SEQ ID NO: 13), (g) perinuclear targeted GEPII 1.0 (SEQ ID NO: 13) by fusing it to the C-terminus of emerin and (h) CAAX-GEPII 1.0 ("GEPII 1.0" disclosed as SEQ ID NO: 13) to monitor $K^+$ in the subplasmalemmal area. The images show that the polypeptide is located in the targeted organelle or subdomain of the cell.

Respective DNA plasmids encoding GEPII 1.0 (SEQ ID NO: 13) with either N-terminal or C-terminal target sequences were cloned using common molecular biology methods known to the skilled artisan. Experiments targeting the GEPII 1.0 polypeptide (SEQ ID NO: 13) (see FIG. 2) to the nucleus (FIG. 4c), mitochondria (FIG. 4d), the endoplasmic reticulum (ER, FIG. 4e), the cell surface (FIG. 4f), the nuclear envelope (FIG. 4g), and the subplasmalemmal area (FIG. 4h) were analyzed by fluorescence microscopy and the results are shown in FIG. 4. GEPII 1.0 (SEQ ID NO: 13) without any targeting sequence is localized within the cytosol and nucleus (FIG. 4a). Addition of a nuclear export sequence (NES; LPPLERLTL (SEQ ID NO: 24)) to the C-terminus of GEPII 1.0 (SEQ ID NO: 13) resulted in localization of the K+ probe within the cytosol only (FIG. 4b). The targeted probes will allowed time laps fluorescence imaging of subcellular $K^+$ fluxes.

10. Characterization of Isolated Polypeptides

Figure 5:
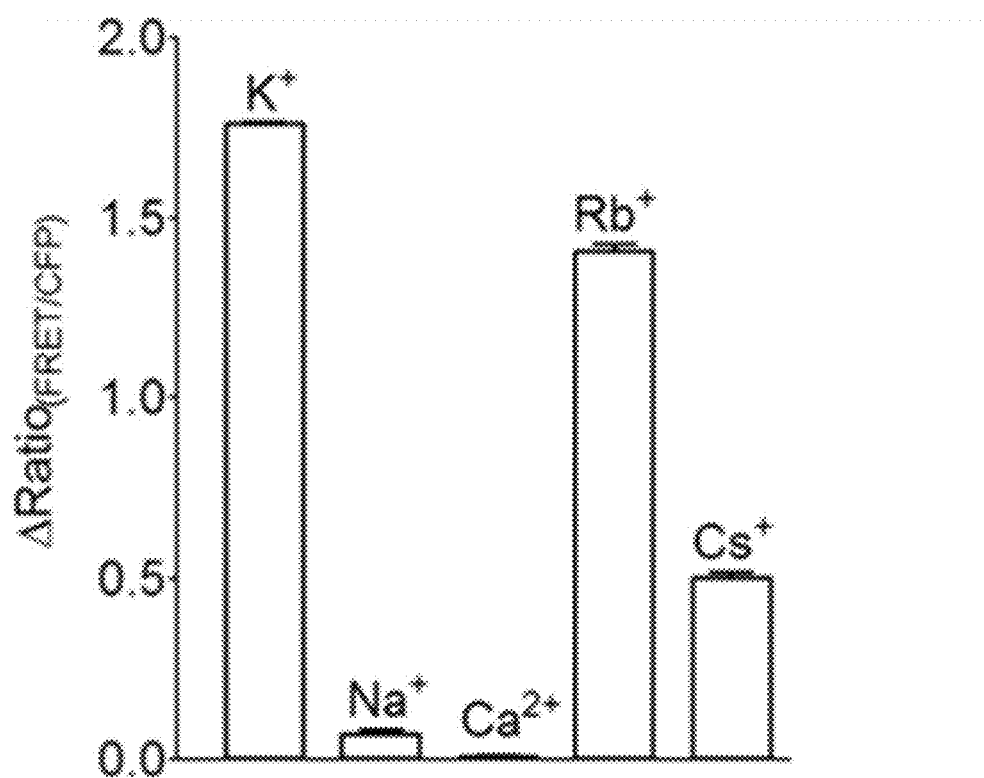
FIG. 5 shows the maximal delta FRET-ratio signals of purified GEPII 1.0 (SEQ ID NO: 13) in response to 3 mM $K^+$, $Na^+$, $Ca^{2+}$, $Rb^+$ or $Cs^+$, respectively. The highest ratio was obtained for $K^+$. $Na^+$ and $Ca^{2+}$ showed the lowest ratios. Experiments were performed using the CLARIOstar fluorescence micro plate reader (BMG Labtech, Germany). 200 nM of purified GEPII in HEPES buffered solution (pH: 7.3) containing 0.05% triton X 100 was analyzed in the absence or presence of either 3 mM KCl, NaCl, $CaCl_2$, RbCl, or CsCl. 80 µl of the GEPII containing solutions were transferred into a multi-well plate (96 well for fluorescence analysis, Greiner Bio-One, Kremsmünster, Austria) and illuminated at 430 nm±10 nm. Emissions were collected at 475 nm±10 nm and 525 nm±10 nm, respectively. FRET ratio values ($F_{525}/F_{475}$) were calculated and correlated with respective FRET ratio values of GEPII in the absence of mono- and divalent ions.

The different GEPII variants were cloned into a petM11 bacterial expression vector. After transformation of the bacterial expression plasmids encoding for GEPIIs into chemical competent DH5α bacteria, cells were cultured on LB agar plates to receive single colonies. Pre-cultures containing single colonies were cultivated overnight and then inoculated in 1 L fresh LB media at 37° C. When an optical density of 0.7 was observed protein expression was induced by adding IPTG (isopropyl β-D-1-thiogalactopyranoside) to a final concentration of 0.5 mM and cells were further cultured at room temperature. Expressed GEPIIs were then extracted from bacteria cells by cell lysis and further purified using affinity chromatography. Elution from columns was obtained with imidazole. GEPII containing eluates were diluted in HEPES buffered solution containing triton X 100 (0.05%). Size exclusion chromatography was further used to confirm recombinant GEPII extraction. Using FRET measurements on a fluorescence plate reader showed that the FRET ratio signal of the recombinant polypeptide was not affected by $Na^+$ and $Ca^{2+}$. In contrast, $K^+$ over $Rb^+$ and $Cs^+$ increased the FRET ratio signal of the purified GEPIIs in response to the addition of 3 mM of the respective ions (see FIG. 5).

11. Determining $K^+$ Concentration in Biological Sample

Figure 6:
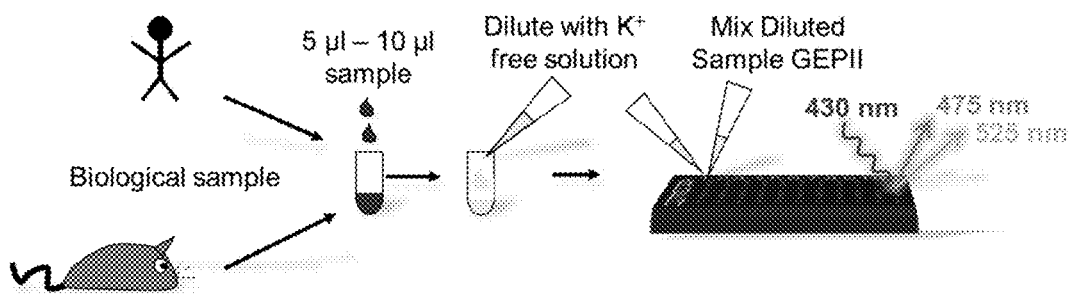
FIG. 6 illustrates possible applications for the polypeptide of the present invention. The concentration of potassium in a small biological sample (e.g. human or mouse sample) may be diluted with a $K^+$-free buffer and the polypeptide of the present invention is then added and the concentration of potassium ions is detected by FRET, e.g. in a multi-well plate (A). Purified GEPII was used to determine the $K^+$ serum concentration in small blood samples (~30 µl) taken either from the vena facealis or orbita (B) of laboratory mice without scarifying the animals. $K^+$ serum levels were determined from respective GEPII FRET ratio values using the linear calibration fit shown in panel C. As depicted, the calibration curve was obtained using 6 defined $K^+$ concentrations in HEPES buffered solution. Mice sera were diluted 1: 12.5 with HEPES buffer and mixed with GEPII solution in a 96 well yielding a final dilution of 1: 25. FRET ratio signals of these samples were measured using the CLARIOstar fluorescence micro plate reader (BMG Labtech, Germany). (D) $K^+$ serum values in mM determined using purified GEPII 1.0 (SEQ ID NO: 13) of 4 different mice, from which blood was either collected from the vena facealis (red circles) or orbita (blue squares). The mode of blood collection did not affect the $K^+$ values. (E) Results shown in panel D are plotted depending on the mode of blood collection. (F) $K^+$ values determined with purified GEPII 1.0 (SEQ ID NO: 13) in 5 different mice sera shortly after blood collection (0 hours), 2- and 4 hours thereafter. This data show that GEPII 1.0 (SEQ ID NO: 13) remains functional in mice sera for hours. (G) Results shown in panel F are plotted depending on the time of FRET measurement after blood collection.
Figure 6:
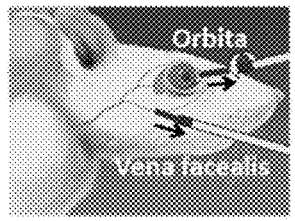
Figure 6:
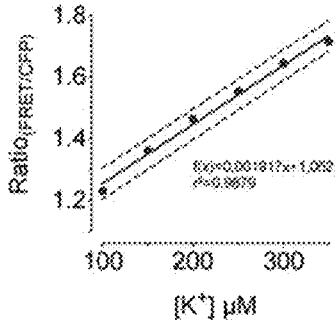
Figure 6:
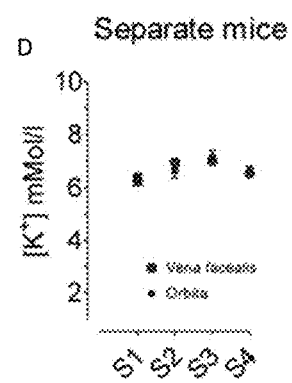
Figure 6:
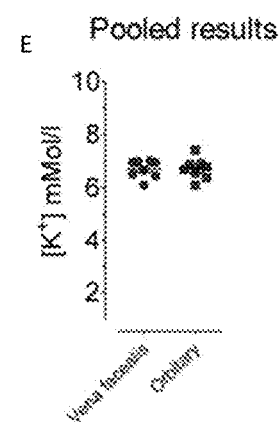
Figure 6:
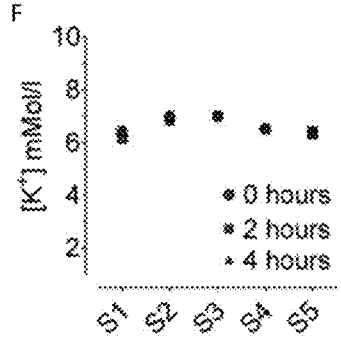
Figure 6:
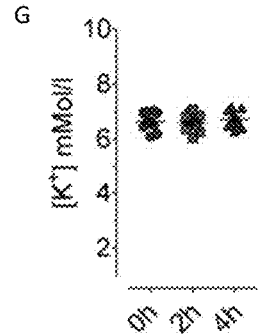

In a preliminary set of experiments we used purified GEPII 1.0 (SEQ ID NO: 13) as described above to determine $K^+$ in mice sera in an experimental setup as described in FIG. 6A. We determined a serum $K^+$ concentration of 6.63±0.34 mM (SD; n=5; FIG. 6) which is well in line with published data. Importantly, the reproducibility and repeatability independently of the mode of blood collection (vena facealis or orbita) as well as the stability of GEPII within mice sera were extremely high (FIG. 6), indicating that GEPII-based determination of $K^+$ in biological probes represents a robust and precise method.

12. Viability/Cell Death Assay

Figure 7:
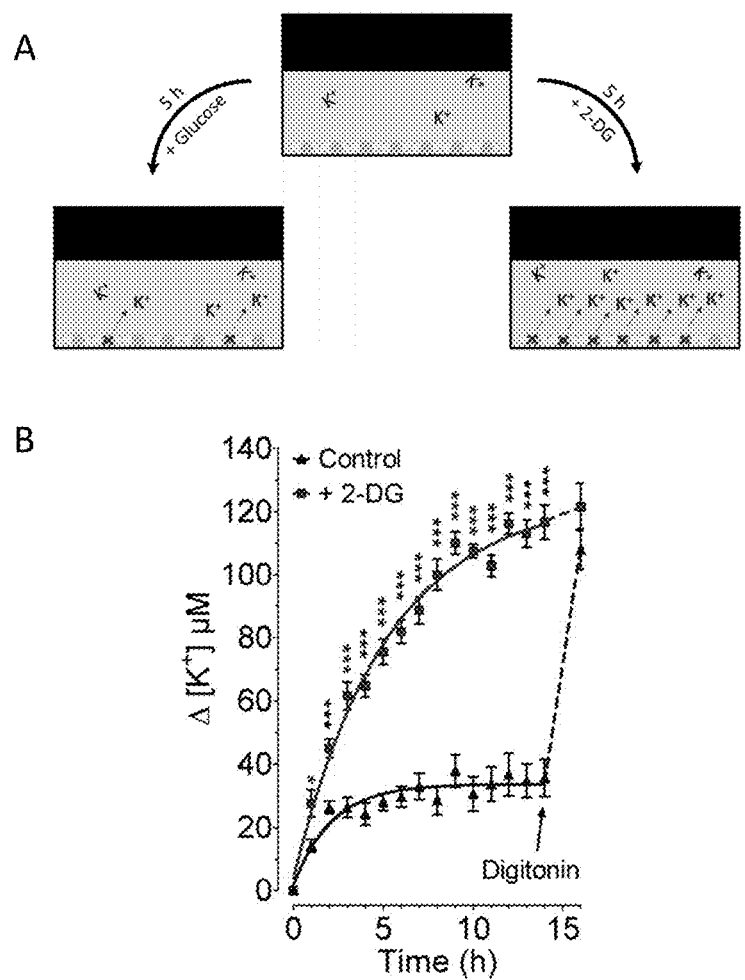
FIG. 7 Panel A schematically illustrates the usage of purified GEPII to dynamically record extracellular $K^+$ concentration over time in a (multi-well) cell culture plate as an energetic measure of cell viability. Cells supplied with substrate such as glucose survive and maintain a physiological $K^+$ gradient with ~5 mM $K^+$ extracellular and ~130 mM $K^+$ intracellular. Under these conditions only few cells die and release $K^+$. In contrast cells treated with toxic antimetabolites such as 2-deoxyglucose (2-DG) die and release $K^+$, which consequently increases in the supernatant. (B) $K^+$ concentration over time of the extracellular medium measured in a 96 well using purified GEPII 1.0 (SEQ ID NO: 13) (c=500 nM). Clonal pancreatic beta cells (INS-1) were kept in the presence of 10 mM glucose (blue curve, control), or 10 mM 2-DG (red curve). As indicated, control cells were treated with 50 µM digitonin at time point 14 hours which maximally released cellular $K^+$. GEPII FRET ratio signals were determined using the CLARIOstar fluorescence micro plate reader (BMG Labtech, Germany) as described above.

Moreover, purified GEPII 1.0 (SEQ ID NO: 13) was used to dynamically record the extracellular $K^+$ concentration in a (multi-well) cell culture plate as a measure of cell viability and cell death. The FRET ratio signal of extracellularly located recombinant GEPII 1.0 (SEQ ID NO: 13) was measured every hour while cells were either kept in a glucose or 2-deoxyglucose (2-DG)-containing culture medium. As shown in FIG. 7, the extracellular $K^+$ concentration in the supernatant of control cells in the presence of 10 mM glucose remained constant over time until cells were permeabilized with 50 μM digitonin. In contrast, the FRET ratio signal of purified GEPII 1.0 (SEQ ID NO: 13) strongly increased over time, if cells were treated with 2-DG, indicating a metabolic crisis, which rapidly leads to loss of intracellular $K^+$. These findings further emphasize that measuring the $K^+$ release of cells in culture represent a real-time read-out of cellular viability.

The invention claimed is:

1. A polypeptide comprising
   a) a first signaling domain, and
   b) a potassium sensor comprising
      1) a first domain of the potassium sensor comprising an amino acid sequence which exhibits at least 70% identity to the sequence according to SEQ ID NO: 1; and
      2) a second domain of the potassium sensor comprising an amino acid sequence which exhibits at least 70% identity to the sequence according to SEQ ID NO: 2;
   wherein the potassium sensor is capable of binding positively charged potassium ion and the first signaling domain is capable of generating a detectable signal upon binding of positively charged potassium ion to the potassium sensor, wherein the polypeptide does not consist of SEQ ID NO:3.

2. A polypeptide according to claim 1 comprising
   a) a first signaling domain, and
   b) a potassium sensor comprising
      1) a first domain of the potassium sensor comprising an amino acid sequence which exhibits at least 70% identity to the sequence according to SEQ ID NO: 1; and
      2) a second domain of the potassium sensor comprising an amino acid sequence which exhibits at least 70% identity to the sequence according to SEQ ID NO: 2; and
   c) a second signaling domain,
   wherein the potassium sensor is capable of binding positively charged potassium ion and the first signaling domain and the second signaling domain together are capable of generating a detectable signal upon binding of positively charged potassium ion to the potassium sensor.

3. The polypeptide of claim 1, wherein the potassium sensor comprises an amino acid sequence for the first domain of the potassium sensor of SEQ ID NO: 1 having at least one of the following amino acid substitutions: D41N, D43N, D51N, D59N, E64Q, D83N, D84N, Q26R, N35Q, N75Q, or G52D, wherein the numbering of amino acid substitutions is based on SEQ ID NO:3.

4. The polypeptide of claim 3, wherein the potassium sensor comprises an amino acid sequence for the first domain of the potassium sensor of SEQ ID NO: 1 having the following substitutions: Q26R, N35Q, N75Q, G52D, wherein the numbering of amino acid substitutions is based on SEQ ID NO:3.

5. The polypeptide of claim 1, wherein the potassium sensor comprises an amino acid sequence for the second domain of the potassium sensor of SEQ ID NO: 2 having at least one of the following amino acid substitutions: D104N, E125Q, D135N, N116Q, N118Q, N121Q or N127Q, wherein the numbering of amino acid substitutions is based on SEQ ID NO:3.

6. The polypeptide of claim 5, wherein the potassium sensor comprises an amino acid sequence of the second domain of the potassium sensor of SEQ ID NO: 2 having the following substitutions: D104N, E125Q, D135N, wherein the numbering of amino acid substitutions is based on SEQ ID NO:3.

7. The polypeptide of claim 1, wherein the polypeptide further comprises at least one linker amino acid sequence -GGGG- (SEQ ID NO:22) or at least one linker sequence of formula (I)

$$-(GGS)_x(GGGGS)_y(GG)_z- \quad \text{(I) (SEQ ID NO: 23)}$$

wherein
x is the integer 0 or 1,
y is an integer from 1 to 6,
z is the integer 0 or 1.

8. The polypeptide of claim 7, wherein y is 2, 3 or 5.

9. The polypeptide of claim 7, wherein the linker amino acid sequence is preceded by the amino acid sequence of the first domain of the potassium sensor and followed by the second domain of the potassium sensor.

10. The polypeptide of claim 2, wherein the first signaling domain and the second signaling domain are together selected from the group consisting of a fluorescence resonance energy transfer (FRET)-donor-acceptor pairs, split-enzyme pairs or split-fluorescent protein pairs, wherein the first signaling domain and the second signaling domain are the respective parts of a pair, wherein the first signaling domain and the second signaling domain are a FRET-donor-acceptor pair.

11. The polypeptide of claim 2, wherein the FRET-donor-acceptor pair is cyan fluorescent protein (CFP) domain and yellow fluorescent protein (YFP) domain comprising circularly permuted venus (CPV).

12. The polypeptide of claim 2, wherein the FRET-donor-acceptor pair is Clover and mRuby2.

13. The polypeptide of claim 1, wherein the first signaling domain is a fluorescent protein domain.

14. A kit for detecting positively charged potassium ions comprising at least one of:
   a) a polypeptide according to claim 1.

15. A method for detecting positively charged potassium ions in a sample, comprising the steps of
   a) providing a polypeptide according to any one of claim 1;
   b) contacting the polypeptide with the sample;
   c) measuring the signal generated by the first signaling domain; and/or
   d) measuring the signal generated together by the first signaling domain and a second signaling domain;

wherein a change in signal intensity after contact with the sample indicates the presence of the potassium ions in the sample.

16. The method of claim 15, wherein the signal measured in step c) and/or d) is a fluorescence signal, a colorimetric signal or a FRET signal.

17. The method of claim 15, wherein the measured signal is a FRET signal.

18. The method of claim 17, wherein the FRET signal is measured after excitation with light at a wavelength in the range of from about 470 nm to about 490 nm and/or an emission of light in the range of from about 510 nm to 520 nm and 590 nm to about 610 nm.

19. The method of claim 15, wherein in step a) the providing of the polypeptide comprises (i) transfecting at least one eukaryotic cell outside the human or animal body or transforming a prokaryotic cell with a polynucleotide encoding the polypeptide of claim 1.

* * * * *

SEQUENCE LISTING

<160> NUMBER OF SEQ ID NOS: 26

<210> SEQ ID NO 1
<211> LENGTH: 63
<212> TYPE: PRT
<213> ORGANISM: Escherichia coli

<400> SEQUENCE: 1

```
Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
            20                  25                  30

Gly Asp Gly Leu Ser Gln Glu Ala Lys Glu Lys Ile Leu Val Ala Val
        35                  40                  45

Gly Asn Ile Ser Gly Ile Ala Ser Val Asp Asp Gln Val Lys Thr
    50                  55                  60
```

<210> SEQ ID NO 2
<211> LENGTH: 50
<212> TYPE: PRT
<213> ORGANISM: Escherichia coli

<400> SEQUENCE: 2

```
Gln Phe Tyr Thr Val Lys Ser Gly Asp Thr Leu Ser Ala Ile Ser Lys
1               5                   10                  15

Gln Val Tyr Gly Asn Ala Asn Leu Tyr Asn Lys Ile Phe Glu Ala Asn
            20                  25                  30

Lys Pro Met Leu Lys Ser Pro Asp Lys Ile Tyr Pro Gly Gln Val Leu
        35                  40                  45
```

Arg Ile
    50

<210> SEQ ID NO 3
<211> LENGTH: 149
<212> TYPE: PRT
<213> ORGANISM: Escherichia coli

<400> SEQUENCE: 3

Met Gly Leu Phe Asn Phe Val Lys Asp Ala Gly Glu Lys Leu Trp Asp
1               5                   10                  15

Ala Val Thr Gly Gln His Asp Lys Asp Gln Ala Lys Lys Val Gln
            20                  25                  30

Glu His Leu Asn Lys Thr Gly Ile Pro Asp Ala Asp Lys Val Asn Ile
        35                  40                  45

Gln Ile Ala Asp Gly Lys Ala Thr Val Thr Gly Asp Gly Leu Ser Gln
    50                  55                  60

Glu Ala Lys Glu Lys Ile Leu Val Ala Val Gly Asn Ile Ser Gly Ile
65                  70                  75                  80

Ala Ser Val Asp Asp Gln Val Lys Thr Ala Thr Pro Ala Thr Ala Ser
                85                  90                  95

Gln Phe Tyr Thr Val Lys Ser Gly Asp Thr Leu Ser Ala Ile Ser Lys
            100                 105                 110

Gln Val Tyr Gly Asn Ala Asn Leu Tyr Asn Lys Ile Phe Glu Ala Asn
        115                 120                 125

Lys Pro Met Leu Lys Ser Pro Asp Lys Ile Tyr Pro Gly Gln Val Leu
    130                 135                 140

Arg Ile Pro Glu Glu
145

<210> SEQ ID NO 4
<211> LENGTH: 50
<212> TYPE: PRT
<213> ORGANISM: Artificial Sequence
<220> FEATURE:
<223> OTHER INFORMATION: LysM D104N,E125Q,D135N

<400> SEQUENCE: 4

Gln Phe Tyr Thr Val Lys Ser Gly Asn Thr Leu Ser Ala Ile Ser Lys
1               5                   10                  15

Gln Val Tyr Gly Asn Ala Asn Leu Tyr Asn Lys Ile Phe Gln Ala Asn
            20                  25                  30

Lys Pro Met Leu Lys Ser Pro Asn Lys Ile Tyr Pro Gly Gln Val Leu
        35                  40                  45

Arg Ile
    50

<210> SEQ ID NO 5
<211> LENGTH: 63
<212> TYPE: PRT
<213> ORGANISM: Artificial Sequence
<220> FEATURE:
<223> OTHER INFORMATION: BON Q26R,N35Q, N75Q, G52D

<400> SEQUENCE: 5

Gln Ala Lys Lys Val Gln Glu His Leu Gln Lys Thr Gly Ile Pro Asp
1               5                   10                  15

Ala Asp Lys Val Asn Ile Gln Ile Ala Asp Asp Lys Ala Thr Val Thr
            20                  25                  30

```
Gly Asp Gly Leu Ser Gln Glu Ala Lys Glu Lys Ile Leu Val Ala Val
            35                  40                  45
Gly Gln Ile Ser Gly Ile Ala Ser Val Asp Asp Gln Val Lys Thr
        50                  55                  60
```

<210> SEQ ID NO 6
<211> LENGTH: 228
<212> TYPE: PRT
<213> ORGANISM: Artificial Sequence
<220> FEATURE:
<223> OTHER INFORMATION: mseCFP

<400> SEQUENCE: 6

```
Met Val Ser Lys Gly Glu Glu Leu Phe Thr Gly Val Val Pro Ile Leu
1               5                   10                  15
Val Glu Leu Asp Gly Asp Val Asn Gly His Arg Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
    50                  55                  60
Leu Thr Trp Gly Val Gln Cys Phe Ala Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Ile Ser His Asn Val Tyr Ile Thr Ala Asp Lys Gln Lys Asn
145                 150                 155                 160
Gly Ile Lys Ala His Phe Lys Ile Arg His Asn Ile Glu Asp Gly Gly
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Lys Leu
        195                 200                 205
Ser Lys Asp Pro Asn Glu Lys Arg Asp His Met Val Leu Leu Glu Phe
    210                 215                 220
Val Thr Ala Ala
225
```

<210> SEQ ID NO 7
<211> LENGTH: 245
<212> TYPE: PRT
<213> ORGANISM: Artificial Sequence
<220> FEATURE:
<223> OTHER INFORMATION: cpV

<400> SEQUENCE: 7

```
Met Asp Gly Gly Val Gln Leu Ala Asp His Tyr Gln Gln Asn Thr Pro
1               5                   10                  15
Ile Gly Asp Gly Pro Val Leu Leu Pro Asp Asn His Tyr Leu Ser Tyr
            20                  25                  30
Gln Ser Lys Leu Ser Lys Asp Pro Asn Glu Lys Arg Asp His Met Val
```

```
                35                  40                  45
Leu Leu Glu Phe Val Thr Ala Ala Gly Ile Thr Leu Gly Met Asp Glu
     50                  55                  60
Leu Tyr Lys Gly Gly Ser Gly Gly Met Val Ser Lys Gly Glu Glu Leu
 65                  70                  75                  80
Phe Thr Gly Val Val Pro Ile Leu Val Glu Leu Asp Gly Asp Val Asn
                 85                  90                  95
Gly His Lys Phe Ser Val Ser Gly Glu Gly Glu Gly Asp Ala Thr Tyr
                100                 105                 110
Gly Lys Leu Thr Leu Lys Leu Ile Cys Thr Thr Gly Lys Leu Pro Val
            115                 120                 125
Pro Trp Pro Thr Leu Val Thr Thr Leu Gly Tyr Gly Leu Gln Cys Phe
        130                 135                 140
Ala Arg Tyr Pro Asp His Met Lys Gln His Asp Phe Phe Lys Ser Ala
145                 150                 155                 160
Met Pro Glu Gly Tyr Val Gln Glu Arg Thr Ile Phe Phe Lys Asp Asp
                165                 170                 175
Gly Asn Tyr Lys Thr Arg Ala Glu Val Lys Phe Glu Gly Asp Thr Leu
            180                 185                 190
Val Asn Arg Ile Glu Leu Lys Gly Ile Asp Phe Lys Glu Asp Gly Asn
        195                 200                 205
Ile Leu Gly His Lys Leu Glu Tyr Asn Tyr Asn Ser His Asn Val Tyr
    210                 215                 220
Ile Thr Ala Asp Lys Gln Lys Asn Gly Ile Lys Ala Asn Phe Lys Ile
225                 230                 235                 240
Arg His Asn Ile Glu
                245

<210> SEQ ID NO 8
<211> LENGTH: 251
<212> TYPE: PRT
<213> ORGANISM: Artificial Sequence
<220> FEATURE:
<223> OTHER INFORMATION: Glover

<400> SEQUENCE: 8

Met Val Ser Lys Gly Glu Glu Leu Phe Thr Gly Val Val Pro Ile Leu
 1               5                  10                  15
Val Glu Leu Asp Gly Asp Val Asn Gly His Lys Phe Ser Val Arg Gly
                20                  25                  30
Glu Gly Glu Gly Asp Ala Thr Asn Gly Lys Leu Thr Leu Lys Phe Ile
            35                  40                  45
Cys Thr Thr Gly Lys Leu Pro Val Pro Trp Pro Thr Leu Val Thr Thr
    50                  55                  60
Phe Gly Tyr Gly Val Ala Cys Phe Ser Arg Tyr Pro Asp His Met Lys
 65                  70                  75                  80
Gln His Asp Phe Phe Lys Ser Ala Met Pro Glu Gly Tyr Val Gln Glu
                85                  90                  95
Arg Thr Ile Ser Phe Lys Asp Asp Gly Thr Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Phe Asn Ser His Asn Val Tyr Ile Thr Ala Asp Lys Gln Lys Asn
```

145                 150                 155                 160
        Gly Ile Lys Ala Asn Phe Lys Ile Arg His Asn Val Glu Asp Gly Ser
                        165                 170                 175

Val Gln Leu Ala Asp His Tyr Gln Gln Asn Thr Pro Ile Gly Asp Gly
                        180                 185                 190

Pro Val Leu Leu Pro Asp Asn His Tyr Leu Ser His Gln Ser Ala Leu
                        195                 200                 205

Ser Lys Asp Pro Asn Glu Lys Arg Asp His Met Val Leu Leu Glu Phe
                        210                 215                 220

Val Thr Ala Ala Gly Ile Thr His Gly Met Asp Glu Leu Tyr Lys Ser
        225                 230                 235                 240

Arg Gly Pro Tyr Ser Ile Val Ser Pro Lys Cys
                        245                 250

<210> SEQ ID NO 9
<211> LENGTH: 237
<212> TYPE: PRT
<213> ORGANISM: Artificial Sequence
<220> FEATURE:
<223> OTHER INFORMATION: mRuby2

<400> SEQUENCE: 9

Met Val Ser Lys Gly Glu Glu Leu Ile Lys Glu Asn Met Arg Met Lys
1               5                   10                  15

Val Val Met Glu Gly Ser Val Asn Gly His Gln Phe Lys Cys Thr Gly
                20                  25                  30

Glu Gly Glu Gly Asn Pro Tyr Met Gly Thr Gln Thr Met Arg Ile Lys
            35                  40                  45

Val Ile Glu Gly Gly Pro Leu Pro Phe Ala Phe Asp Ile Leu Ala Thr
        50                  55                  60

Ser Phe Met Tyr Gly Ser Arg Thr Phe Ile Lys Tyr Pro Lys Gly Ile
65                  70                  75                  80

Pro Asp Phe Phe Lys Gln Ser Phe Pro Glu Gly Phe Thr Trp Glu Arg
                85                  90                  95

Val Thr Arg Tyr Glu Asp Gly Gly Val Val Thr Val Met Gln Asp Thr
            100                 105                 110

Ser Leu Glu Asp Gly Cys Leu Val Tyr His Val Gln Val Arg Gly Val
        115                 120                 125

Asn Phe Pro Ser Asn Gly Pro Val Met Gln Lys Lys Thr Lys Gly Trp
    130                 135                 140

Glu Pro Asn Thr Glu Met Met Tyr Pro Ala Asp Gly Gly Leu Arg Gly
145                 150                 155                 160

Tyr Thr His Met Ala Leu Lys Val Asp Gly Gly His Leu Ser Cys
                165                 170                 175

Ser Phe Val Thr Thr Tyr Arg Ser Lys Lys Thr Val Gly Asn Ile Lys
            180                 185                 190

Met Pro Gly Ile His Ala Val Asp His Arg Leu Glu Arg Leu Glu Glu
        195                 200                 205

Ser Asp Asn Glu Met Phe Val Val Gln Arg Glu His Ala Val Ala Lys
    210                 215                 220

Phe Ala Gly Leu Gly Gly Gly Met Asp Glu Leu Tyr Lys
225                 230                 235

<210> SEQ ID NO 10
<211> LENGTH: 189
<212> TYPE: DNA

<213> ORGANISM: Escherichia coli

<400> SEQUENCE: 10

```
caggcgaaga aggtgcagga gcatctgaac aaaaccggta taccggatgc cgataaagtg      60
aatattcaaa ttgccgacgg caaagcgacg gtcactggtg acggcctgag tcaggaggcg     120
aaggagaaaa tccttgttgc ggtggggaat atttccggta ttgccagtgt cgatgatcag     180
gtgaaaacg                                                             189
```

<210> SEQ ID NO 11
<211> LENGTH: 150
<212> TYPE: DNA
<213> ORGANISM: Escherichia coli

<400> SEQUENCE: 11

```
cagttttata ccgttaagtc tggcgacact ctgagtgcca tttccaaaca ggtctacggt      60
aacgctaatc tgtacaataa aatcttcgaa gcgaataaac cgatgctaaa agcccggat      120
aaaatttatc cggggcaagt gttgcgtatt                                      150
```

<210> SEQ ID NO 12
<211> LENGTH: 447
<212> TYPE: DNA
<213> ORGANISM: Escherichia coli

<400> SEQUENCE: 12

```
atgggtctgt tcaattttgt gaaagatgcc ggagaaaaac tctgggacgc ggttacaggt      60
cagcacgata aagacgatca ggcgaagaag gtgcaggagc atctgaacaa aaccggtata     120
ccggatgccg ataaagtgaa tattcaaatt gccgacggca agcgacggt cactggtgac     180
ggcctgagtc aggaggcgaa ggagaaaatc cttgttgcgg tggggaatat ttccggtatt     240
gccagtgtcg atgatcaggt gaaaacggcg acaccagcca ctgccagcca gttttatacc     300
gttaagtctg cgacactct gagtgccatt tccaaacagg tctacggtaa cgctaatctg     360
tacaataaaa tcttcgaagc gaataaaccg atgctaaaaa gcccggataa aatttatccg     420
gggcaagtgt tgcgtattcc ggaagag                                         447
```

<210> SEQ ID NO 13
<211> LENGTH: 626
<212> TYPE: PRT
<213> ORGANISM: Artificial Sequence
<220> FEATURE:
<223> OTHER INFORMATION: GEP II 1.0

<400> SEQUENCE: 13

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
```

```
                100             105             110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
    195                 200                 205

Ser Lys Asp Pro Asn Glu Lys Arg Asp His Met Val Leu Leu Glu Phe
210                 215                 220

Val Thr Ala Ala Ile Asp Met Gly Leu Phe Asn Phe Val Lys Asp Ala
225                 230                 235                 240

Gly Glu Lys Leu Trp Asp Ala Val Thr Gly Gln His Asp Lys Asp Asp
                245                 250                 255

Gln Ala Lys Lys Val Gln Glu His Leu Asn Lys Thr Gly Ile Pro Asp
            260                 265                 270

Ala Asp Lys Val Asn Ile Gln Ile Ala Asp Gly Lys Ala Thr Val Thr
    275                 280                 285

Gly Asp Gly Leu Ser Gln Glu Ala Lys Glu Lys Ile Leu Val Ala Val
290                 295                 300

Gly Asn Ile Ser Gly Ile Ala Ser Val Asp Asp Gln Val Lys Thr Ala
305                 310                 315                 320

Thr Pro Ala Thr Ala Ser Gln Phe Tyr Thr Val Lys Ser Gly Asp Thr
                325                 330                 335

Leu Ser Ala Ile Ser Lys Gln Val Tyr Gly Asn Ala Asn Leu Tyr Asn
            340                 345                 350

Lys Ile Phe Glu Ala Asn Lys Pro Met Leu Lys Ser Pro Asp Lys Ile
    355                 360                 365

Tyr Pro Gly Gln Val Leu Arg Ile Pro Glu Glu Phe Met Asp Gly
370                 375                 380

Gly Val Gln Leu Ala Asp His Tyr Gln Gln Asn Thr Pro Ile Gly Asp
385                 390                 395                 400

Gly Pro Val Leu Leu Pro Asp Asn His Tyr Leu Ser Tyr Gln Ser Lys
                405                 410                 415

Leu Ser Lys Asp Pro Asn Glu Lys Arg Asp His Met Val Leu Leu Glu
            420                 425                 430

Phe Val Thr Ala Ala Gly Ile Thr Leu Gly Met Asp Glu Leu Tyr Lys
    435                 440                 445

Gly Gly Ser Gly Gly Met Val Ser Lys Gly Glu Glu Leu Phe Thr Gly
450                 455                 460

Val Val Pro Ile Leu Val Glu Leu Asp Gly Asp Val Asn Gly His Lys
465                 470                 475                 480

Phe Ser Val Ser Gly Glu Gly Glu Gly Asp Ala Thr Tyr Gly Lys Leu
                485                 490                 495

Thr Leu Lys Leu Ile Cys Thr Thr Gly Lys Leu Pro Val Pro Trp Pro
            500                 505                 510

Thr Leu Val Thr Thr Leu Gly Tyr Gly Leu Gln Cys Phe Ala Arg Tyr
    515                 520                 525
```

```
Pro Asp His Met Lys Gln His Asp Phe Phe Lys Ser Ala Met Pro Glu
    530                 535                 540

Gly Tyr Val Gln Glu Arg Thr Ile Phe Phe Lys Asp Asp Gly Asn Tyr
545                 550                 555                 560

Lys Thr Arg Ala Glu Val Lys Phe Glu Gly Asp Thr Leu Val Asn Arg
                565                 570                 575

Ile Glu Leu Lys Gly Ile Asp Phe Lys Glu Asp Gly Asn Ile Leu Gly
                580                 585                 590

His Lys Leu Glu Tyr Asn Tyr Asn Ser His Asn Val Tyr Ile Thr Ala
                595                 600                 605

Asp Lys Gln Lys Asn Gly Ile Lys Ala Asn Phe Lys Ile Arg His Asn
    610                 615                 620

Ile Glu
625

<210> SEQ ID NO 14
<211> LENGTH: 127
<212> TYPE: PRT
<213> ORGANISM: Artificial Sequence
<220> FEATURE:
<223> OTHER INFORMATION: GEPII 2.7

<400> SEQUENCE: 14

Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
                20                  25                  30

Gly Asp Gly Leu Ser Gln Glu Ala Lys Glu Lys Ile Leu Val Ala Val
            35                  40                  45

Gly Asn Ile Ser Gly Ile Ala Ser Val Asp Asp Gln Val Lys Thr Ala
        50                  55                  60

Thr Pro Ala Thr Ala Ser Gly Gly Gly Ser Gly Gly Gln Phe Tyr
65                  70                  75                  80

Thr Val Lys Ser Gly Asn Thr Leu Ser Ala Ile Ser Lys Gln Val Tyr
                85                  90                  95

Gly Asn Ala Asn Leu Tyr Asn Lys Ile Phe Gln Ala Asn Lys Pro Met
                100                 105                 110

Leu Lys Ser Pro Asn Lys Ile Tyr Pro Gly Gln Val Leu Arg Ile
            115                 120                 125

<210> SEQ ID NO 15
<211> LENGTH: 130
<212> TYPE: PRT
<213> ORGANISM: Artificial Sequence
<220> FEATURE:
<223> OTHER INFORMATION: GEPII 2.10

<400> SEQUENCE: 15

Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
                20                  25                  30

Gly Asp Gly Leu Ser Gln Glu Ala Lys Glu Lys Ile Leu Val Ala Val
            35                  40                  45

Gly Asn Ile Ser Gly Ile Ala Ser Val Asp Asp Gln Val Lys Thr Ala
        50                  55                  60

Thr Pro Ala Thr Ala Ser Gly Gly Gly Gly Ser Gly Gly Gly Gly Ser
```

65                  70                  75                  80
Gln Phe Tyr Thr Val Lys Ser Gly Asn Thr Leu Ser Ala Ile Ser Lys
                85                  90                  95

Gln Val Tyr Gly Asn Ala Asn Leu Tyr Asn Lys Ile Phe Gln Ala Asn
            100                 105                 110

Lys Pro Met Leu Lys Ser Pro Asn Lys Ile Tyr Pro Gly Gln Val Leu
        115                 120                 125

Arg Ile
    130

<210> SEQ ID NO 16
<211> LENGTH: 135
<212> TYPE: PRT
<213> ORGANISM: Artificial Sequence
<220> FEATURE:
<223> OTHER INFORMATION: GEPII 2.15

<400> SEQUENCE: 16

Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
            20                  25                  30

Gly Asp Gly Leu Ser Gln Glu Ala Lys Glu Lys Ile Leu Val Ala Val
        35                  40                  45

Gly Asn Ile Ser Gly Ile Ala Ser Val Asp Asp Gln Val Lys Thr Ala
    50                  55                  60

Thr Pro Ala Thr Ala Ser Gly Gly Gly Ser Gly Gly Gly Ser
65                  70                  75                  80

Gly Gly Gly Gly Ser Gln Phe Tyr Thr Val Lys Ser Gly Asn Thr Leu
                85                  90                  95

Ser Ala Ile Ser Lys Gln Val Tyr Gly Asn Ala Asn Leu Tyr Asn Lys
            100                 105                 110

Ile Phe Gln Ala Asn Lys Pro Met Leu Lys Ser Pro Asn Lys Ile Tyr
        115                 120                 125

Pro Gly Gln Val Leu Arg Ile
    130                 135

<210> SEQ ID NO 17
<211> LENGTH: 142
<212> TYPE: PRT
<213> ORGANISM: Artificial Sequence
<220> FEATURE:
<223> OTHER INFORMATION: GEPII 2.22

<400> SEQUENCE: 17

Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
            20                  25                  30

Gly Asp Gly Leu Ser Gln Glu Ala Lys Glu Lys Ile Leu Val Ala Val
        35                  40                  45

Gly Asn Ile Ser Gly Ile Ala Ser Val Asp Asp Gln Val Lys Thr Ala
    50                  55                  60

Thr Pro Ala Thr Ala Ser Gly Gly Gly Ser Gly Gly Gly Ser
65                  70                  75                  80

Gly Gly Gly Gly Ser Gly Gly Gly Ser Gly Gly Gln Phe Tyr Thr
                85                  90                  95

Val Lys Ser Gly Asn Thr Leu Ser Ala Ile Ser Lys Gln Val Tyr Gly
            100                 105                 110

Asn Ala Asn Leu Tyr Asn Lys Ile Phe Gln Ala Asn Lys Pro Met Leu
        115                 120                 125

Lys Ser Pro Asn Lys Ile Tyr Pro Gly Gln Val Leu Arg Ile
    130                 135                 140

<210> SEQ ID NO 18
<211> LENGTH: 148
<212> TYPE: PRT
<213> ORGANISM: Artificial Sequence
<220> FEATURE:
<223> OTHER INFORMATION: GEP II 2.28

<400> SEQUENCE: 18

Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
            20                  25                  30

Gly Asp Gly Leu Ser Gln Glu Ala Lys Glu Lys Ile Leu Val Ala Val
        35                  40                  45

Gly Asn Ile Ser Gly Ile Ala Ser Val Asp Asp Gln Val Lys Thr Ala
    50                  55                  60

Thr Pro Ala Thr Ala Ser Gly Gly Ser Gly Gly Gly Ser Gly Gly
65                  70                  75                  80

Gly Gly Ser Gly Gly Gly Ser Gly Gly Gly Ser Gly Gly
            85                  90                  95

Gly Ser Gln Phe Tyr Thr Val Lys Ser Gly Asn Thr Leu Ser Ala Ile
            100                 105                 110

Ser Lys Gln Val Tyr Gly Asn Ala Asn Leu Tyr Asn Lys Ile Phe Gln
        115                 120                 125

Ala Asn Lys Pro Met Leu Lys Ser Pro Asn Lys Ile Tyr Pro Gly Gln
    130                 135                 140

Val Leu Arg Ile
145

<210> SEQ ID NO 19
<211> LENGTH: 124
<212> TYPE: PRT
<213> ORGANISM: Artificial Sequence
<220> FEATURE:
<223> OTHER INFORMATION: GEPII 2.4

<400> SEQUENCE: 19

Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
            20                  25                  30

Gly Asp Gly Leu Ser Gln Glu Ala Lys Glu Lys Ile Leu Val Ala Val
        35                  40                  45

Gly Asn Ile Ser Gly Ile Ala Ser Val Asp Asp Gln Val Lys Thr Ala
    50                  55                  60

Thr Pro Ala Thr Ala Ser Gly Gly Gly Gln Phe Tyr Thr Val Lys
65                  70                  75                  80

Ser Gly Asn Thr Leu Ser Ala Ile Ser Lys Gln Val Tyr Gly Asn Ala
            85                  90                  95

Asn Leu Tyr Asn Lys Ile Phe Gln Ala Asn Lys Pro Met Leu Lys Ser
        100                 105                 110

```
Pro Asn Lys Ile Tyr Pro Gly Gln Val Leu Arg Ile
        115                 120

<210> SEQ ID NO 20
<211> LENGTH: 127
<212> TYPE: PRT
<213> ORGANISM: Artificial Sequence
<220> FEATURE:
<223> OTHER INFORMATION: GEPII 2.7

<400> SEQUENCE: 20

Gln Ala Lys Lys Val Gln Glu His Leu Asn Lys Thr Gly Ile Pro Asp
1               5                   10                  15

Ala Asp Lys Val Asn Ile Gln Ile Ala Asp Gly Lys Ala Thr Val Thr
            20                  25                  30

Gly Asp Gly Leu Ser Gln Glu Ala Lys Glu Lys Ile Leu Val Ala Val
        35                  40                  45

Gly Asn Ile Ser Gly Ile Ala Ser Val Asp Asp Gln Val Lys Thr Ala
    50                  55                  60

Thr Pro Ala Thr Ala Ser Gly Gly Gly Ser Gly Gly Gln Phe Tyr
65                  70                  75                  80

Thr Val Lys Ser Gly Asn Thr Leu Ser Ala Ile Ser Lys Gln Val Tyr
                85                  90                  95

Gly Asn Ala Asn Leu Tyr Asn Lys Ile Phe Gln Ala Asn Lys Pro Met
            100                 105                 110

Leu Lys Ser Pro Asn Lys Ile Tyr Pro Gly Gln Val Leu Arg Ile
        115                 120                 125

<210> SEQ ID NO 21
<211> LENGTH: 641
<212> TYPE: PRT
<213> ORGANISM: Artificial Sequence
<220> FEATURE:
<223> OTHER INFORMATION: R-GEPII 1.0

<400> SEQUENCE: 21

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Val Ala Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
```

```
              165                 170                 175
Val Gln Leu Ala Asp His Tyr Gln Gln Asn Thr Pro Ile Gly Asp Gly
                180                 185                 190

Pro Val Leu Leu Pro Asp Asn His Tyr Leu Ser His Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr His Gly Met Asp Glu Leu Tyr Lys Ser
225                 230                 235                 240

Arg Gly Pro Tyr Ser Ile Val Ser Pro Lys Cys Ile Asp Met Gly Leu
                245                 250                 255

Phe Asn Phe Val Lys Asp Ala Gly Glu Lys Leu Trp Asp Ala Val Thr
            260                 265                 270

Gly Gln His Asp Lys Asp Gln Ala Lys Lys Val Gln Glu His Leu
        275                 280                 285

Asn Lys Thr Gly Ile Pro Asp Ala Asp Lys Val Asn Ile Gln Ile Ala
        290                 295                 300

Asp Gly Lys Ala Thr Val Thr Gly Asp Gly Leu Ser Gln Glu Ala Lys
305                 310                 315                 320

Glu Lys Ile Leu Val Ala Val Gly Asn Ile Ser Gly Ile Ala Ser Val
                325                 330                 335

Asp Asp Gln Val Lys Thr Ala Thr Pro Ala Thr Ala Ser Gln Phe Tyr
            340                 345                 350

Thr Val Lys Ser Gly Asp Thr Leu Ser Ala Ile Ser Lys Gln Val Tyr
        355                 360                 365

Gly Asn Ala Asn Leu Tyr Asn Lys Ile Phe Glu Ala Asn Lys Pro Met
        370                 375                 380

Leu Lys Ser Pro Asp Lys Ile Tyr Pro Gly Gln Val Leu Arg Ile Pro
385                 390                 395                 400

Glu Glu Glu Phe Met Val Ser Lys Gly Glu Glu Leu Ile Lys Glu Asn
                405                 410                 415

Met Arg Met Lys Val Val Met Glu Gly Ser Val Asn Gly His Gln Phe
            420                 425                 430

Lys Cys Thr Gly Glu Gly Glu Gly Asn Pro Tyr Met Gly Thr Gln Thr
        435                 440                 445

Met Arg Ile Lys Val Ile Glu Gly Gly Pro Leu Pro Phe Ala Phe Asp
        450                 455                 460

Ile Leu Ala Thr Ser Phe Met Tyr Gly Ser Arg Thr Phe Ile Lys Tyr
465                 470                 475                 480

Pro Lys Gly Ile Pro Asp Phe Phe Lys Gln Ser Phe Pro Glu Gly Phe
                485                 490                 495

Thr Trp Glu Arg Val Thr Arg Tyr Glu Asp Gly Gly Val Val Thr Val
            500                 505                 510

Met Gln Asp Thr Ser Leu Glu Asp Gly Cys Leu Val Tyr His Val Gln
        515                 520                 525

Val Arg Gly Val Asn Phe Pro Ser Asn Gly Pro Val Met Gln Lys Lys
        530                 535                 540

Thr Lys Gly Trp Glu Pro Asn Thr Glu Met Met Tyr Pro Ala Asp Gly
545                 550                 555                 560

Gly Leu Arg Gly Tyr Thr His Met Ala Leu Lys Val Asp Gly Gly Gly
                565                 570                 575

His Leu Ser Cys Ser Phe Val Thr Thr Tyr Arg Ser Lys Lys Thr Val
            580                 585                 590
```

```
Gly Asn Ile Lys Met Pro Gly Ile His Ala Val Asp His Arg Leu Glu
        595                 600                 605

Arg Leu Glu Glu Ser Asp Asn Glu Met Phe Val Val Gln Arg Glu His
    610                 615                 620

Ala Val Ala Lys Phe Ala Gly Leu Gly Gly Met Asp Glu Leu Tyr
625                 630                 635                 640

Lys

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly
1

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(3)
<223> OTHER INFORMATION: This region may encompass 0-1 "Gly Gly Ser"
      repeating units
<220> FEATURE:
<221> NAME/KEY: MISC_FEATURE
<222> LOCATION: (4)..(33)
<223> OTHER INFORMATION: This region may encompass 1-6 "Gly Gly Gly Gly
      Ser" repeating units
<220> FEATURE:
<221> NAME/KEY: MISC_FEATURE
<222> LOCATION: (34)..(35)
<223> OTHER INFORMATION: This region may encompass 0-1 "Gly Gly"
      repeating units

<400> SEQUENCE: 23

Gly Gly Ser Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly
        35

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Pro Pro Leu Glu Arg Leu Thr Leu
1               5

<210> SEQ ID NO 25
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 25

Lys Arg Ser Trp Ser Met Ala Phe Cys
1               5

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Ser Lys Asp Val Lys Lys Lys Lys Lys Ser Lys Thr Lys Cys
1               5                   10                  15

Val Ile Met
```